United States Patent
Scarborough et al.

(10) Patent No.: US 8,524,907 B2
(45) Date of Patent: Sep. 3, 2013

(54) METHODS OF SYNTHESIZING PHARMACEUTICAL SALTS OF A FACTOR XA INHIBITOR

(75) Inventors: Robert M. Scarborough, Half Moon Bay, CA (US); Carroll Scarborough, legal representative, Half Moon Bay, CA (US); James P Kanter, San Carlos, CA (US); Keiko Sujino, Edmonton (CA); Sharique Sami Zuberi, Folsom, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 863 days.

(21) Appl. No.: 12/446,954

(22) PCT Filed: Nov. 1, 2007

(86) PCT No.: PCT/US2007/083394
§ 371 (c)(1),
(2), (4) Date: Feb. 24, 2010

(87) PCT Pub. No.: WO2008/057972
PCT Pub. Date: May 15, 2008

(65) Prior Publication Data
US 2010/0197929 A1 Aug. 5, 2010

Related U.S. Application Data

(60) Provisional application No. 60/864,145, filed on Nov. 2, 2006.

(51) Int. Cl.
C07D 213/74 (2006.01)
C07D 215/38 (2006.01)

(52) U.S. Cl.
USPC .................. 546/155; 546/159; 546/309

(58) Field of Classification Search
USPC ............. 564/159, 155, 309; 546/159, 155, 546/309
See application file for complete search history.

(56) References Cited

U.S. PATENT DOCUMENTS

| | | | |
|---|---|---|---|
| 2,095,619 A | 10/1937 | Stoesser | |
| 4,514,416 A | 4/1985 | Fujii et al. | |
| 4,588,587 A | 5/1986 | Gasic | |
| 4,912,001 A | 3/1990 | Kouno et al. | |
| 4,971,957 A | 11/1990 | Tsutsumi et al. | |
| 5,569,768 A | 10/1996 | Boyd et al. | |
| 5,576,343 A | 11/1996 | Nagahara et al. | |
| 5,872,115 A | 2/1999 | Binet et al. | |
| 6,140,351 A | 10/2000 | Arnaiz et al. | |
| 6,376,515 B2 | 4/2002 | Zhu et al. | |
| 6,627,646 B2 | 9/2003 | Bakale et al. | |
| 6,632,815 B2 | 10/2003 | Zhu et al. | |
| 6,642,224 B1 | 11/2003 | Hirayama et al. | |
| 6,686,368 B1 | 2/2004 | Zhu et al. | |
| 6,720,317 B1 | 4/2004 | Song et al. | |
| 6,835,739 B2 | 12/2004 | Zhu et al. | |
| 6,844,367 B1 | 1/2005 | Zhu et al. | |
| 7,022,695 B2 | 4/2006 | Zhu et al. | |
| 7,285,565 B2 | 10/2007 | Zhu et al. | |
| 7,307,074 B2 | 12/2007 | Hirayama et al. | |
| 7,312,235 B2 | 12/2007 | Zhu et al. | |
| 7,314,874 B2 | 1/2008 | Zhu et al. | |
| 7,342,013 B2 | 3/2008 | Zhu et al. | |
| 7,521,470 B2 | 4/2009 | Zhu et al. | |
| 7,598,276 B2 | 10/2009 | Grant et al. | |
| 7,696,352 B2 | 4/2010 | Zhu et al. | |
| 7,727,981 B2 | 6/2010 | Zhu et al. | |
| 7,727,982 B2 | 6/2010 | Zhu et al. | |
| 2003/0162690 A1 | 8/2003 | Zhu et al. | |
| 2007/0259924 A1 | 11/2007 | Song et al. | |
| 2008/0153876 A1 | 6/2008 | Sinha et al. | |
| 2008/0254036 A1 | 10/2008 | Sinha et al. | |
| 2008/0279845 A1 | 11/2008 | Conley et al. | |
| 2008/0293704 A1 | 11/2008 | Jia et al. | |
| 2009/0030045 A1 | 1/2009 | Song et al. | |
| 2009/0186810 A1 | 7/2009 | Zwaal et al. | |
| 2010/0063113 A1 | 3/2010 | Grant et al. | |

FOREIGN PATENT DOCUMENTS

| | | |
|---|---|---|
| CH | 520 657 | 3/1972 |
| EP | 077 534 | 4/1983 |
| EP | 0 540 051 | 5/1993 |
| EP | 0 798 295 | 10/1997 |
| EP | 0 937 711 | 8/1999 |

(Continued)

OTHER PUBLICATIONS

Cundiff et al., Anayltical Chemistry, vol. 28, No. 5, May 1956, pp. 792-797.*

(Continued)

*Primary Examiner* — Rebecca Anderson
(74) *Attorney, Agent, or Firm* — Foley & Lardner LLP

(57) ABSTRACT

Novel methods of preparing a compound of Formula I which is an inhibitor of Factor Xa and its maleate salt, are described herein.

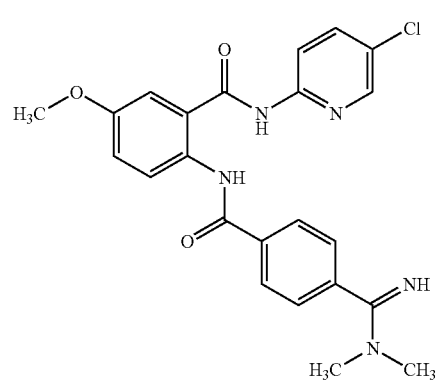

23 Claims, No Drawings

(56) References Cited

FOREIGN PATENT DOCUMENTS

| | | |
|---|---|---|
| GB | 1 047 245 | 11/1966 |
| GB | 2 220 206 | 1/1990 |
| JP | 59-181257 | 10/1984 |
| JP | 11-302177 | 11/1999 |
| WO | WO 94/13693 | 6/1994 |
| WO | WO 94/28427 | 12/1994 |
| WO | WO 97/21437 | 6/1997 |
| WO | WO 97/29067 | 8/1997 |
| WO | WO 98/06694 | 2/1998 |
| WO | WO 98/09630 | 3/1998 |
| WO | WO 98/28269 | 7/1998 |
| WO | WO 98/28282 | 7/1998 |
| WO | WO 98/57934 | 12/1998 |
| WO | WO 99/00121 | 1/1999 |
| WO | WO 99/00126 | 1/1999 |
| WO | WO 99/00127 | 1/1999 |
| WO | WO 99/00128 | 1/1999 |
| WO | WO 99/10316 | 3/1999 |
| WO | WO 99/07379 | 7/1999 |
| WO | WO 99/32477 | 7/1999 |
| WO | WO 99/42439 | 8/1999 |
| WO | WO 00/07980 | 2/2000 |
| WO | WO 00/34237 | 6/2000 |
| WO | WO 00/34238 | 6/2000 |
| WO | WO 00/34258 | 6/2000 |
| WO | WO 00/34260 | 6/2000 |
| WO | WO 00/34261 | 6/2000 |
| WO | WO 00/34268 | 6/2000 |
| WO | WO 00/34269 | 6/2000 |
| WO | WO 00/39118 | 7/2000 |
| WO | WO 01/19788 | 3/2001 |
| WO | WO 01/64642 | 9/2001 |
| WO | WO 01/64643 | 9/2001 |
| WO | WO 2007/056517 | 5/2007 |

OTHER PUBLICATIONS

U.S. Appl. No. 12/446,954, filed Feb. 24, 2010, Scarborough et al.
U.S. Appl. No. 12/756,037, filed Apr. 7, 2010, Zhu et al.
Bachmann, W.E. et al., "Reduction by Magnesium + Magnesium Halide, XIII. The Reaction Between Epoxy Ketones and Grignard Reagents", *Journal of the American Chemical Society*, vol. 56, No. 7, pp. 1559-1560 (1934).
Berge, S.M. et al., "Pharmaceutical Salts", *Journal of Pharmaceutical Science*, vol. 66, No. 1, pp. 1-19 (1997).
Brittain H.G. et al., "Polymorphism in Pharmaceutical Solids", *Marcel Dekker, Inc.*, pp. 1-2 and pp. 183-226 (1999).
Cheng, Y. et al., "Relationship between the Inhibition Constant (KI) and the Concentration of Inhibitor Which Causes 50 Percent Inhibition (I50) of an Enzymatic Reaction", *Biochemical Pharmacology*, vol. 22, pp. 3099-3108 (1973).
Claeson, G., "Synthetic Peptides and Peptidomimetics as Substrates and Inhibitors of Thrombin and Other Proteases in the Blood Coagulation System", *Blood Coagulation and Fibrinolysis*, vol. 5, pp. 411-436 (1994).
"CMU Seed Fund Project on Detection and Control of Pharmaceutical Polymorphism," *The Department of Carnegie Mellon*, Internet, pp. 1-3 (2002).
Cockburn, W.F. et al., "Molecular Rearrangement of Tertiary Amines. Part I", *J. Org. Chem.*, pp. 3340-3346 (1960).
Concise Encyclopedia Chemistry, NY: Walter de Gruyter Berlin, pp. 872-873 (1994).
Dictionary of Organic Compounds, 5$^{th}$ Ed., vol. 5, Chapman and Hall, New York, NY, US, compounds T-00160-T-00162, p. 5119 (1982).
Doelker,E, "Séance Thematique Modifications Cristallines et Transformations Polymorphes Au Cours Des Operations Galeniques," *Ann. Pharm. Fr.*, vol. 60, pp. 161-176 (2002)(Not in the English language).
Doelker, E., "Caracteres Physicochimiques Des Principes Actifs Leurs Consequences Sur La Faisabilite Et La Stabilite Des Formers Galeniques," *STP Pharma Pratiques*, vol. 9, No. 5, pp. 399-409 (1999) (Not in the English language).
Elodi, s. et al., "Optimization of Conditions for the Catalytic Effect of the Factor IXa-Factor VIII Complex: Probable Role of the Complex in the Amplification of Blood Coagulation," *Thrombosis Research*, vol. 15, pp. 617-629 (1979).
El-Zanfally, S., "Condensation of Acetanthranil and Phenylanthranil with Certain Aminoheterocycles. Attempted Preparation of Some 2,3-Disubstituted 4 (3H0-Quinazolinones," *Egypt. J. Pharm. Sci.*, vol. 17, No. 1, pp. 29-34 (1978).
Finlayson, K. et al., "[3H]dofetilide Binding to HERG Transfected Membranes: A Potential High Throughput Preclinical Screen,"European Journal of Pharamcology, vol. 430, pp. 147-148 (2001).
Gresele, P. et al., "Novel approaches to the Treatment of Thrombosis", *Trends in Pharmacological Sciences*, vol. 23, No. 1, pp. 25-32 (2002).
Hamilton, A., "Intra- and Intermolecular Hydrogen Bonding Control of Supermolecular Structure", *Department in Chemistry, Computational Approaches in Supramolecular Chemistry*, vol. 426, pp. 101-108 (1994).
Hauptmann, J., et al., "Comparison of the Anticoagulant and Antithrombotic Effects of Synthetic Thrombin and Factor Xa Inhibitors," *Thrombosis and Haemostasis*, vol. 63, pp. 220-223 (1990).
Haverkamp, W. et al., "The Potential for QT Prolongation and Pro-Arrhythmia by Non-Anti-Arrhythmic Drugs: Clinical and Regulatory Implications. Report on a Policy Conference of the European Society of Cardiology", *Cardiovascular Research*, vol. 47, pp. 219-233 (2000).
Herron, D.K., et al., "1,2-Dibenzamidobenzene Inhibitors of Human Factor Xa", *J. Med. Chem.*, vol. 43, pp. 859-872 (2000).
Hey, D.H. et al., "Internuclear Cyclisation. Part XXI. Thermal Decomposition of Diazonium Sulphates from Alkoxy-N-alkyl-2-aminobenzanilides," *J. Chem. Soc.*, vol. 16, pp. 1513-1518 (1967).
Hitomi, Y., et al., "Inhibitory Effect of New Synthetic Protease Inhibitor (FUT-175) on the Coagulation System", *Haemostasis*, vol. 15, pp. 164-168 (1985).
Jain, N.K. et al., Polymorphism in Pharmacy, *Indian Drugs*, vol. 23, No. 6, pp. 315-329 (1986).
Kam, C. et al., "Mechanism Based Isocoumarin Inhibitors for Trypsin and Blood Coagulation Serine Protease: New Anticoagulants", *Biochemistry*, vol. 27, pp. 2547-2557 (1988).
Keumi, T. et al., "2-(Trifluoromethylsulfonyloxy)pyridine as a Reagent for the Ketone Synthesis from Carboxylic Acids and Aromatic Hydrocarbons", *Bull. Chem. Soc. Jpn.*, vol. 61, pp. 455-459 (1988).
Kuhn, R. et al., "Addition von Maleinsaure-anhydrid an Polyene. (Uber konjugierte Doppelbindungen, XIV", *Berichte Der Deutschen Chemischen, Gesellschaft*, vol. 63, pp. 2662-2679 (1930) (Not in the English language).
Kulkarni, Y.D., "Possible Antifertility Agents. Part-1. Synthesis of 2-(N,N-Substituted-amininomethyl)-3-(2-pyridyl)-4(3H)-oxo3,I-quinazolines," *J. Indian Chem. Soc.*, vol. LX1, pp. 720-721 (1984).
Kuzmic, P. et al., "High-throughput Screening of Enzyme Inhibitors: Automatic Determination of Tight-Binding Inhibition Constants", Analytical Biochemistry, vol. 281, pp. 62-67 (2000).
Muzaffer, N.A. et al., "Polymorphism and Drug Availability,"*Faculty of Pharmacy*, Lahore, Pakistan, vol. 9, No. 1, pp. 59-66 (1979).
Netzer, R. et al., "Screening Lead Compounds for QT Interval Prolongation", *Drug Discovery Today*, vol. 6, No. 2, pp. 78-84 (2001).
Nutt, E. et al., "The Amino Acid Sequence of Antistatin, a Potent Inhibitor of Factor Xa Reveals a Repeated Internal Structure", *The Journal of Biological Chemistry*, vol. 263, No. 21, pp. 10162-10167 (1988).
Otsuka, M. et al., "Effect of Polymorphic Forms of Bulk Powders on Pharmaceutical Properties of Carbamazepine Granules," *Chem. Pharm. Bull.*, vol. 47, No. 6, pp. 852-856 (1999).
Pearlstein, R. et al., "Characterization of HERG Potassium Channel Inhibition Using CoMSiA 3D QSAR and Homology Modeling Approaches", *Bioorganic & Medicinal Chemistry Letters*, vol. 13, pp. 1829-1835 (2003).
Redfern, W. et al, "Relationships Between Preclinical Cardiac Electrophysiology, Clinical QT Interval Prolongation and Torsade de Pointes for a Broad Range of Drugs: Evidence for a Provisional Safety Margin in Drug Development", *Cardiovascular Research*, vol. 58, pp. 32-45 (2003).

Rouhi, A.M., "The Right Stuff," *Chemical & Engineering News*, pp. 32-35 (2003).

Rowland, M. et al, "Clinical Pharmacokinetics, Concepts and Applications," *College of Pharmacy*, pp. 123-124 (1995).

Silverman, R.B, "The Organic Chemistry of Drug Design and Drug Action," Second Edition, *Academic Press*, pp. 72-76 (1993).

Singhal, D. et al., "Drug Polymorphism and Dosage Form Design: a Practical Perspective," Advanced Drug Delivery Reviews, vol. 56, pp. 335-347 (2004).

Sipe, H.J., Jr. et al., "An Improved Synthesis of Aryl Sulfones", *Synthesis*, No. 3, pp. 283-284 (1984).

St. Goldschmidt et al., "Biphenyl Derivatives II. Basic 4-Biphenyl Compounds", *Recueil*, vol. 69, pp. 1109-1117 (1950).

Sturzebecher, J. et al., "Synthetic Inhibitors of Bovine Factor Xa and Thrombin. Comparison of Their Anticoagulant Efficiency", *Thrombosis Research*, vol. 54, pp. 245-252 (1989).

Suzuki, H. et al., "Selective Reduction with Lithium Aluminum Hydride/Diphosphorous Tetraiodide. A Mild Conversion of Aromatic Ketones to Parent Hydrocarbons", *Chemistry Letters*, The Chemical Society of Japan, pp. 909-910 (1983).

Taday, P.F. et al., "Using Terahertz Pulse Spectroscopy to Study the Crystalline Structure of a Drug: A Case Study of the Polymorphs of Ranitidine Hydrochloride," *Journal of Pharmaceutical Sciences*, vol. 92, No. 4, pp. 831-838 (2003).

Tan, K.T. et al., "Factor X Inhibitors", *Expert Opin. Investig. Drugs*, vol. 12, No. 5, pp. 799-804 (2003).

Tidwell, R.R et al., "Strategies for Anticoagulation with Synthetic Protease Inhibitors. Xa Inhibitors Versus Thrombin Inhibitors", Thrombosis Research, vol. 19, pp. 339-349 (1980).

Turner, A. et al., "p-Amidino Esters as Irreversible Inhibitors of Factor IXa and Xa and Thrombin", *Biochemistry*,vol. 25, pp. 4929-4935 (1986).

Turpie,A.G., "Future Therapeutic Directins for Factor Xa Inhibition in the Prophylaxis and Treatment of Thromobtic Disorders," *Am. J. Health Syst. Pharm.*, vol. 60, (Suppl. 7), S20-S24 (2003).

"X-Ray Diffraction," *U.S. Pharmacopeial 23, National Formulary* 18, pp. 1843-1844 (1995).

Waxman, L. et al., "Tick Anticoagulant Peptide (TAP) is a novel Inhibitor of Blood Coagulation Factor Xa" *Science Magazine*, vol. 248, pp. 593-596 (1990).

West, A.R., Solid State Chemistry and its Applications, Chapter 10, Solid Solutions, Wiley, New York, pp. 358-365 (1988).

Wiley, M.R. et al., "Structure-Based Design of Potent, Amidine-Derived Inhibitors of Factor Xa: Evaluation of Selectively, Anticoagulant Activity, and Antithrombotic Activity", *J. Med. Chem.*, vol. 43, pp. 883-899 (2000).

Yee, Y.K. et al., "$N^2$-Aroylanthranilamide Inhibitors of Human Factor Xa", *J. Med. Chem.*, vol. 43, pp. 873-882 (2000).

Young, J.D. et al., "Interannular Interactions in Para-Substituted Dipenylmethane Anion Radicals, " *J. Am. Chem. Soc.*, vol. 94, No. 25, pp. 8790-8794 (1972).

Zhou, Z. et al., "Properties of HERG Channels Stably Expressed in HEK293 Cells Studied at Physiological Temperature", Biophysical Journal, vol. 74, pp. 230-241 (1998).

Zhu, B.Y. et al. "Chapter 9. Factor Xa Inhibitors: Recent Advances in Anticoagulant Agents," *Annual Reports in Medicinal Chemistry*, vol. 35, pp. 83-102 (2000).

Jia, et al. 1-(2-Naphthyl)-1H-pyrazole-5-carboxylamides as potent factor Xa inhibitors. Part 2: A survey of P4 motifs. Bioorg Med Chem Lett. Mar. 8, 2004;14(5)1 221-7.

Zhang, et al. Design, synthesis, and SAR of anthranilamide-based factor Xa inhibitors incorporating substituted biphenyl P4 motifs. Bioorg Med Chem Lett. Feb. 23, 2004;14(4):983-7.

\* cited by examiner

METHODS OF SYNTHESIZING PHARMACEUTICAL SALTS OF A FACTOR Xa INHIBITOR

CROSS-REFERENCE TO RELATED APPLICATION

This application is a national stage application under 35 U.S.C. §371 of International Application No. PCT/US2007/083394, filed Nov. 1, 2007, which claims the benefit under 35 U.S.C. §119(e) of U.S. Provisional Patent Application Ser. No. 60/864,145, filed Nov. 2, 2006, which are incorporated herein by reference in their entirety.

BACKGROUND OF THE INVENTION

1. Field of the Invention

This invention is directed to methods for synthesizing Factor Xa inhibitors as well as to the synthesis of the intermediates and maleate salt thereof.

2. State of the Art

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction, or other disruption. Although platelets and blood coagulation are both involved in restoring hemostasis and in thrombotic diseases, certain components of the coagulation cascade are primarily responsible for the amplification and acceleration of the processes involved in platelet aggregation and fibrin deposition which are major events in thrombosis and hemostasis.

Clot formation involves the conversion of fibrinogen to fibrin which polymerizes into a network to restore hemostasis after injury. A similar process results in occluded blood vessels in thrombotic diseases. The conversion of fibrinogen to fibrin is catalyzed by thrombin, the end product of a series of reactions in the blood coagulation cascade. Thrombin is also a key player in activating platelets, thereby contributing to thrombosis under conditions of both arterial and venous blood flow. For these reasons, it has been postulated that efficient regulation of thrombin can lead to efficient regulation of thrombosis. Several classes of currently used anticoagulants directly or indirectly affect thrombin (i.e. unfractionated heparins, low-molecular weight heparins, heparin-like compounds, pentasaccharide and warfarin). Direct or indirect inhibition of thrombin activity has also been the focus of a variety of anticoagulants in clinical development (reviewed by Eriksson and Quinlan, *Drugs* 11: 1411-1429, 2006).

Prothrombin, the precursor for thrombin, is converted to the active enzyme by Factor Xa. Localized activation of tissue factor/Factor VIIa mediated Factor Xa generation is amplified by the Factor IXa/Factor VIIIa complex and leads to prothrombinase assembly on activated platelets. Factor Xa, as a part of the prothrombinase complex, is the sole enzyme responsible for sustained thrombin formation in the vasculature. Factor Xa is a serine protease, the activated form of its precursor Factor X, and a member of the calcium ion binding, gamma carboxyglutamic acid (GLA)-containing, vitamin K dependent, and blood coagulation factors. Unlike thrombin, which acts on a variety of protein substrates including fibrinogen and the PAR receptors (Protease activated receptors, Coughlin, *J Thrombosis Haemostasis* 3: 1800-1814, 2005), Factor Xa appears to have a single physiologic substrate, namely prothrombin. Since one molecule of Factor Xa may be able to generate greater than 1000 molecules of thrombin (Mann, et al., *J. Thrombosis. Haemostasis* 1: 1504-1514, 2003), direct inhibition of Factor Xa as a way of indirectly inhibiting the formation of thrombin may be an efficient anticoagulant strategy. This assertion is based on the key role of prothrombinase in thrombin synthesis and on the fact that inhibition of prothrombinase will have a pronounced effect on the overall platelet aggregation and clotting pathways.

Activated proteases such as Factor VIIa, Factor IXa or Factor Xa have poor proteolytic activity on their own. However, their assembly into cofactor-dependent, membrane-bound complexes significantly enhances their catalytic efficiencies. This effect is most dramatic for Factor Xa, where the efficiency is increased by a factor of $10^5$ (Mann, et al., *Blood* 76(1):1-16, 1990). Due to the higher concentration of the zymogens present in blood (1.4 µM prothrombin versus 150 nM Factor X) and the kinetics of activation, a smaller amount of Factor Xa than thrombin needs to be inhibited to achieve an anticoagulant effect. Indirect proof of the hypothesis of superiority of Factor Xa as a therapeutic target compared to thrombin can also be found in clinical trials for the prevention of deep vein thrombosis. Fondaparinux, an antithrombin III dependent Factor Xa inhibitor, was proven to be superior to enoxaparin (a low molecular weight heparin that inhibits both thrombin and Factor Xa) in four trials of orthopedic surgery (Turpie, et al., *Archives Internal Medicine* 162(16): 1833-1840, 2002). Therefore, it has been suggested that compounds which selectively inhibit Factor Xa may be useful as in vitro diagnostic agents, or for therapeutic administration in certain thrombotic disorders, see e.g., WO 94/13693.

Several Factor Xa inhibitors have been reported as polypeptides derived from hematophagous organisms, as well as compounds which are not large polypeptide-type inhibitors. Additional Factor Xa inhibitors include small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal amidino (—C(=NH)—NH$_2$) group; WO 97/21437 describes benzimidazole compounds substituted by a basic radical which are connected to a naphthyl group via a straight or branched chain alkylene, —C(=O)— or —S(=O)$_2$— bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

Additional reported Factor Xa inhibitors include those having a structure comprising a phenyl-amidino, phenyl, and halo-phenyl connected via amide linkages (U.S. Pat. No. 6,844,367 B1). Other Factor Xa inhibitors have replaced the halo-phenyl with a halo-pyridyl (see U.S. Pat. Nos. 6,376,515 B2 and 6,835,739 B2). U.S. Pat. No. 6,376,515 B2 discloses a specific Factor Xa inhibitor compound identified in Example 206, which is also disclosed in U.S. Pat. No. 6,835,739 B2 as Example 206 and herein identified as a compound of Formula I. The compound of Formula I is represented by the following structure:

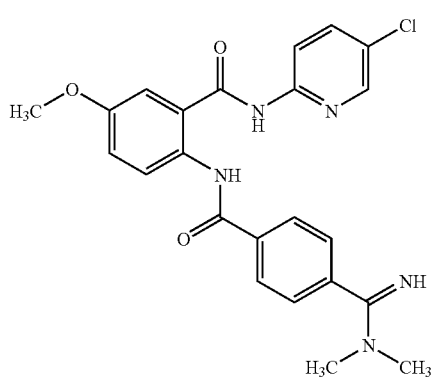

I

Further work in developing selective inhibitors of Factor Xa has led to the surprising discovery that certain salts of this compound exhibit better thermal and hydrolytic stability than the free-base compounds themselves, with the maleate salt, having the best thermal and hydrolytic stability observed. This information may be found in US Patent Publication US2007/0112039).

In light of the relevance of this compound in treating thrombotic diseases, there exists a need in an efficient method of making the compound and relevant intermediates.

SUMMARY OF THE INVENTION

This invention is directed to methods of preparing a compound of Formula I, maleate salt of the compound of Formula I, and intermediates thereof. The methods also include recovery of the products.

In one embodiment, this invention provides a method of preparing a maleate salt of a compound of Formula I:

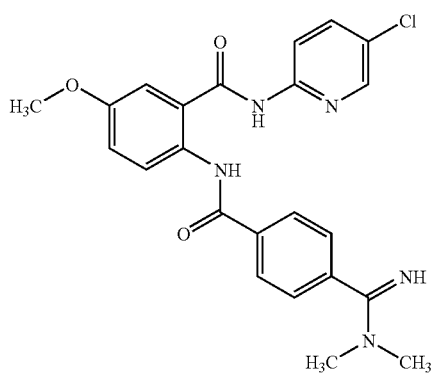

I comprising contacting the compound of Formula I with at least a molar equivalent of maleic acid in a solvent mixture of $C_{1-4}$ alkanol and water at a temperature of between 10° C. and 40° C. under reaction conditions to form the maleate salt of the compound of Formula I.

In another embodiment, this invention provides a method of preparing the maleate salt of a compound of Formula I from the compound of Formula I or the compound of Formula I on a large scale, such as the gram or kilogram scale.

In another embodiment, this invention provides a method of preparing a maleate salt of a compound of Formula I:

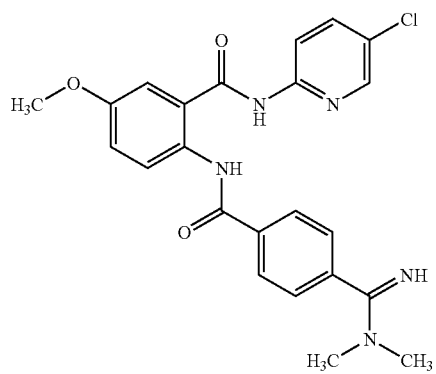

I comprising:

a) contacting a compound of Formula A:

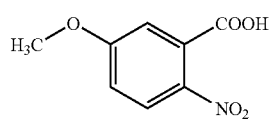

A with a compound of Formula B:

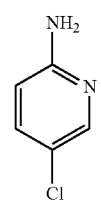

B under reaction conditions to form a compound of Formula C:

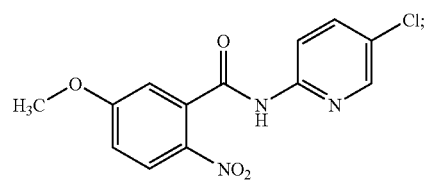

C b) exposing the compound of Formula C to reaction conditions to form a compound of Formula D:

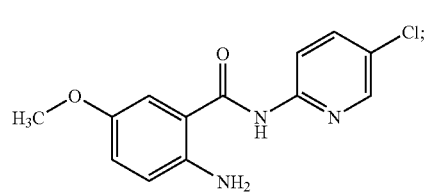

D c) contacting the compound of Formula D with a compound of Formula E:

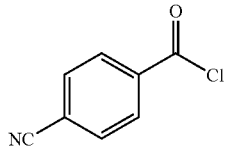

under reaction conditions to form a compound of Formula F:

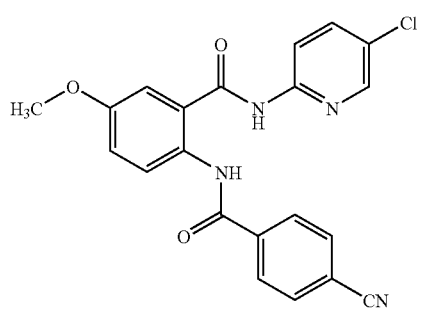

or a salt thereof;
d) contacting LiN(CH$_3$)$_2$ with the compound of Formula F or a salt thereof, under reaction conditions to form the compound of Formula I; and
e) contacting the compound of Formula I with at least a molar equivalent of maleic acid in a solvent mixture of C$_{1-4}$ alkanol and water at a temperature of between 10° C. and 40° C. under reaction conditions to form the maleate salt of the compound of Formula I.

In another embodiment, this invention provides a method of preparing a compound of Formula I:

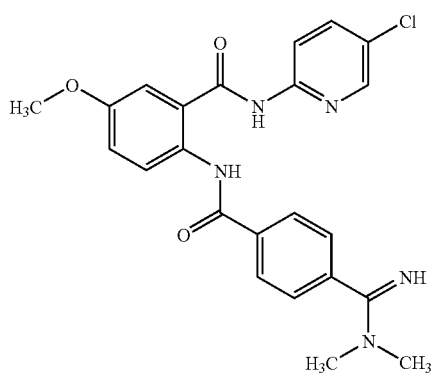

comprising:
a) contacting a compound of Formula A:

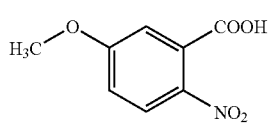

with a compound of Formula B:

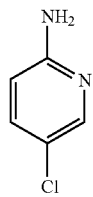

under reaction conditions comprising acetonitrile as a solvent to form a compound of Formula C:

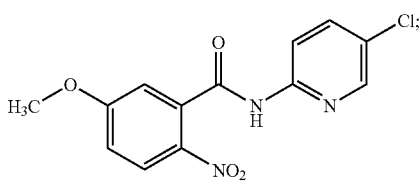

b) exposing the compound of Formula C to reaction conditions to form a compound of Formula D:

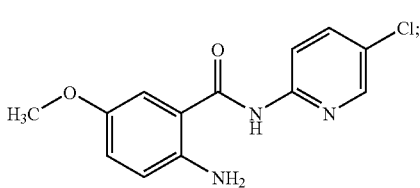

c) contacting the compound of Formula D with a compound of Formula E:

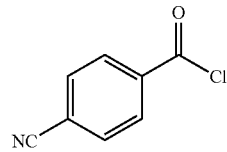

under reaction conditions to form a compound of Formula F:

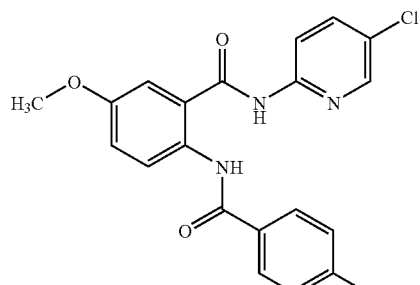

or a salt thereof; and
d) contacting LiN(CH$_3$)$_2$ with the compound of Formula F or a salt thereof, under reaction conditions to form the compound of Formula I.

DETAILED DESCRIPTION OF THE INVENTION

As discussed in U.S. Pat. No. 6,376,515 which is a continuation-in-part of U.S. Pat. No. 6,844,367 (the '367 patent), the compound of Formula I is a potent Xa inhibitor. The present invention involves an improved synthesis of the compound of Formula I, wherein the improvement is over the synthesis reported in U.S. Pat. No. 6,844,367. The present invention also involves conversion of the compound of Formula I to its maleate salt. The maleate salt of the compound of Formula I, has excellent crystallinity, thermal and hydrolytic stability, and purity. The present invention involves the synthesis of the maleate salt on a gram as well as a kilogram scale. The maleate salt of the compound of Formula I, is useful for the treatment of undesired thrombosis in mammals.

I. Definitions

As used in the specification and claims, the singular form "a", "an" and "the" include plural references unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude trace contaminants in the elements and the like. "Consisting of" shall mean excluding more than trace amount of other ingredients and substantial method steps recited. Embodiments defined by each of these transition terms are within the scope of this invention.

As used herein, the term "$C_{1-4}$ alkanol" refers to monovalent saturated aliphatic hydrocarbyl compounds having from 1 to 4 carbon atoms and having one of the hydrogen atoms substituted with a hydroxy (OH) group. Examples of $C_{1-4}$ alkanol include methanol, ethanol, n-propanol, isopropanol, n-butanol, isobutanol, sec-butanol, and t-butanol.

As used herein, the term "contacting" refers to bringing two or more chemical molecules to close proximity so that a reaction between the two or more chemical molecules can occur. For example, contacting may comprise mixing and continuously mixing the chemicals. Contacting may be done by fully or partially dissolving or suspending two or more chemicals in one or more solvents, mixing of a chemical in a solvent with another chemical in solid or gas phase, or mixing two or more solid chemicals, or other methods that are generally known to those skilled in the art.

As used herein, the term "reaction conditions" refers to the details under which a chemical reaction proceeds. Examples of reaction conditions include, but are not limited to, one or more of following: reaction temperature, solvent, pH, pressure, reaction time, mole ratio of reactants, the presence of a base or acid, or catalyst, etc. Reaction conditions may be named after the particular chemical reaction in which the conditions are employed, such as, coupling conditions, hydrogenation conditions, acylation conditions, reduction conditions, salt forming conditions, etc. Reaction conditions for known reactions are generally known to those skilled in the art.

The term "salt formation conditions" or "salt forming conditions" generally refers to conditions used to form a salt between, for example, a compound having a basic group, such as a compound of Formula I with an organic or inorganic acid. Salt forming conditions may include mixing the molecule having the basic group and the acid in a solvent or a mixture of solvents for a period of time under a certain temperature, which would be generally known to a person skilled in the art. Alternatively, the compound can be passed over an ion exchange resin to form the desired salt or one salt form of the product can be converted into another using the same general process. The first salt can then be converted to a second salt such as a maleate salt. Salt forming conditions may also be conditions where the acid is a by-product of a reaction forming the compound whose salt is formed.

The term "coupling conditions" generally refers to conditions used in coupling reactions where two chemical entities are connected to form one chemical entity via a coupling reagent. In some cases, a coupling reaction refers to the reaction connecting a compound bearing an carboxylic acid group to a compound bearing an amino group to form a compound having an amide bond. Coupling conditions generally include a coupling reagent, for example phosphorous oxychloride ($POCl_3$). Common coupling reagents also include, but are not limited to, carbodiimides such as N—N'-dicyclohexylcarbodiimide (DCC), and 1-ethyl-3-(3'-dimethylaminopropyl)carbodiimide (EDCI). The carbodiimides may be used in conjunction with additives such as dimethylaminopyridine (DMAP) or 1-hydroxybenzotriazole (HOBt). Amide coupling reagents also include amininum and phosphonium based reagents, such as N-[(dimethylamino)-1H-1,2,3-triazolo[4,5-b]pyridine-1-ylmethylene]-N-methylmethanaminium hexafluorophosphate N-oxide (HATU), N-[(1H-benzotriazol-1-yl)(dimethylamino)methylene]-N-methylmethanaminium hexafluorophosphate N-oxide (HBTU) and benzotriazol-1-yl-N-oxy-tris(pyrrolidino)phosphonium hexafluorophosphate (PyBOP). Coupling conditions may include a solvent such as dimethylformamide, tetrahydrofuran, dichloromethane, acetonitrile or mixtures thereof, and may also include an organic base such as pyridine, diisopropylethylamine (DIEA), dimethylaminopyridine (DMAP) or mixtures thereof. Coupling conditions may include a temperature of between −10° C. to room temperature.

The term "acylation conditions" generally refers to conditions used in reactions where an acylating reagent, i.e. a compound having an activated acyl group, such as acyl chloride (—C(O)Cl), reacts with another compound, for example a compound having an amino group, to form a new compound where the acylating reagent is connected to the other compound via the carbonyl (—C(O)—) group. Acylation conditions may include a solvent or a mixture of solvents and may also include a base. Acylation conditions may include a temperature of between −10° C. to room temperature.

The term "hydrogenation conditions" generally refers to conditions used in reactions where hydrogen gas reacts with a compound, for example, a nitro compound, to form a new compound, such as an amino compound. Hydrogenation conditions may include hydrogen gas, a catalyst such as palladium, platinum, or sulfided platinum, a solvent or a mixture of solvents and a suitable temperature.

It is to be understood that when a value is recited for a condition or a yield, the value may vary within a reasonable range, such as ±10%, ±5%, and ±1%.

II. Pharmaceutical Compositions

Compounds and salts made by methods of the invention may be used in pharmaceutical compositions. The pharmaceutical compositions of the present invention can be used for preventing or treating a subject suffering from a condition, wherein the condition is characterized by undesired thrombosis. The pharmaceutical compositions of the present invention are comprised of a pharmaceutically acceptable carrier and a therapeutically acceptable amount of a salt of a compound of Formula I, for example, a maleate salt of the compound of Formula I.

A. Pharmaceutically Acceptable Carriers

Diagnostic applications of the maleate salt of the compound of Formula I, typically aqueous solutions or suspensions, will typically utilize formulations such as solutions or suspensions.

In the management of thrombotic disorders the compounds of this invention may be utilized in compositions such as tablets, capsules, lozenges or elixirs for oral administration, suppositories, sterile solutions or suspensions or injectable administration, and the like, or incorporated into shaped articles. Subjects in need of treatment (typically mammalian subjects) can be administered appropriate dosages of the compounds of this invention that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Capsules useful in the present invention can be prepared using conventional and known encapsulation techniques, such as that described in Stroud et al., U.S. Pat. No. 5,735,105. The capsule is typically a hollow shell of generally cylindrical shape having a diameter and length sufficient so that the pharmaceutical solution compositions containing the appropriate dose of the active agent fits inside the capsule. The exterior of the capsules can include plasticizer, water, gelatin, modified starches, gums, carrageenans, and mixtures thereof. Those skilled in the art will appreciate what compositions are suitable.

In addition to the active agent, tablets useful in the present invention can comprise fillers, binders, compression agents, lubricants, disintegrants, colorants, water, talc and other elements recognized by one of skill in the art. The tablets can be homogeneous with a single layer at the core, or have multiple layers in order to realize preferred release profiles. In some instances, the tablets of the instant invention may be coated, such as with an enteric coating. One of skill in the art will appreciate that other excipients are useful in the tablets of the present invention.

Lozenges useful in the present invention include an appropriate amount of the active agent as well as any fillers, binders, disintegrants, solvents, solubilizing agents, sweeteners, coloring agents and any other ingredients that one of skill in the art would appreciate is necessary. Lozenges of the present invention are designed to dissolve and release the active agent on contact with the mouth of the patient. One of skill in the art will appreciate that other delivery methods are useful in the present invention.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium, and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations (such as tablets, capsules and lozenges) and topical formulations such as ointments, drops and dermal patches. The sterile of this invention are desirably incorporated into shaped articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidinone, pyran copolymer, polyhydroxy-propyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

B. Dosing

Typically, about 0.5 to 500 mg of a compound or mixture of compounds of this invention is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

It is contemplated that a typical dosage will range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered once or several times daily, and other dosage regimens may also be useful.

III. Methods

A. Compound Preparation

The compound of Formula I can be converted to salts of various organic and inorganic acids. Some examples of the salt include, but are not limited to, hydrochloric acid salt, lactate, maleate, acetate, phenoxyacetate, propionate, succinate, adipate, ascorbate, camphorate, gluconate, phosphate, tartrate, citrate, mesylate, fumarate, glycolate, naphthalene-1,5-disulfonate, gentisate, benzene sulfonate, camphor sulfonate, α-hydroxycaproate, benzoate, glucuronate, ketoglutarate, malate, malonate, mandelate, pyroglutamate, sulfate, and trans-cinnamate. One of skill in the art will recognize that other acids can be used to make salts of the compound of Formula I using the methods of the present invention. The first salt can then be converted to a second salt such as a maleate salt.

A number of methods are useful for the preparation of the salts described above and are known to those skilled in the art. For example, reaction of the compound of Formula I with one or more equivalents of the desired acid in a solvent or a solvent mixture in which the salt is insoluble, or in a solvent where the solvent is removed by evaporation, distillation or freeze drying. Alternatively, the compound of Formula I can be passed over an ion exchange resin to form the desired salt or one salt form of the product can be converted into another using the same general process.

This invention provides an improved synthesis of the compound of Formula I, wherein the improvement is over the published procedure in the U.S. Pat. No. 6,844,367. Preparation of the maleate salt of the compound of Formula I, is also described below.

In one embodiment, the maleate salt of the compound of Formula I is represented by the following structure:

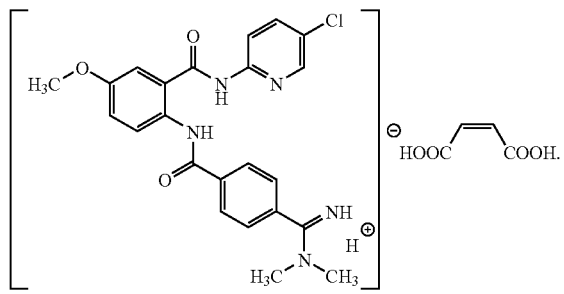

In another embodiment, this invention provides a method of preparing a maleate salt of a compound of Formula I:

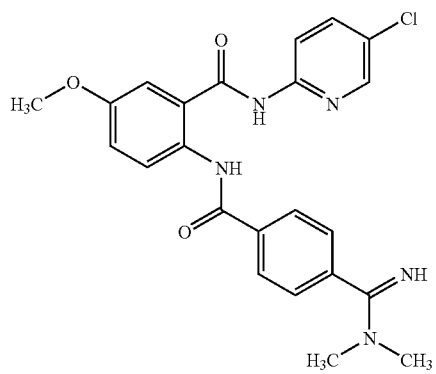

comprising contacting the compound of Formula I with at least a molar equivalent of maleic acid in a solvent mixture of $C_{1-4}$ alkanol and water at a temperature of between 10° C. and 40° C. under reaction conditions to form the maleate salt of the compound of Formula I.

In another embodiment, the reaction conditions comprise a temperature of between 19° C. and 25° C. In one embodiment, the solvent mixture is a mixture of methanol and water. In another embodiment, the solvent mixture is a mixture of ethanol and water. In yet another embodiment, the solvent mixture is a mixture of methanol, ethanol and water. In another embodiment, the solvent mixture of ethanol and water is in a ratio of about 2:1 to about 8:1. In another embodiment, the solvent mixture of ethanol and water is in a ratio of about 3.5:1 to about 4.5:1. In another embodiment, the solvent mixture of ethanol and water is in a ratio of about 1:1 to 0:1.

In another embodiment, the process further comprises recovering the maleate salt. In one embodiment, the maleate salt is recovered from a solvent mixture of ethanol and water in a ratio of about 1:1 to 0:1.

In another embodiment, the maleate salt of the compound of Formula I is afforded in a yield of at least 65%. In a preferred embodiment, the maleate salt of the compound of Formula I is afforded in a yield of at least 75%. In another preferred embodiment, the maleate salt of the compound of Formula I is afforded in a yield of at least 85%. In another embodiment, this invention provides a method of preparing a maleate salt of a compound of Formula I from a compound of Formula I on a kilogram scale.

In another embodiment, this invention provides a method of preparing a maleate salt of a compound of Formula I:

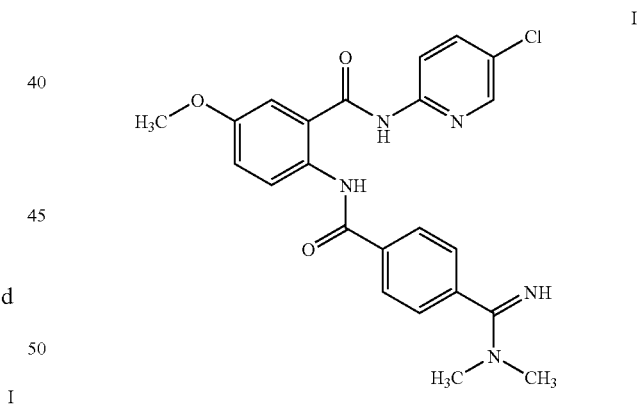

comprising (1) forming a salt of the compound of Formula I with an organic or an inorganic acid that is not maleic acid, and (2) converting the salt of the compound of Formula I to a maleate salt of the compound of Formula I. Some examples of the salt include, but are not limited to, HCl salt, lactate, acetate, phenoxyacetate, propionate, succinate, adipate, ascorbate, camphorate, gluconate, phosphate, tartrate, citrate, mesylate, fumarate, glycolate, naphthalene-1,5-disulfonate, gentisate, benzene sulfonate, camphor sulfonate, benzoate, glucuronate, α-hydroxycaproate, ketoglutarate, malate, malonate, mandelate, sulfate, pyroglutamate, and trans-cinnamate. One of skill in the art will recognize that other acids can be used to make salts of the compound of Formula I using the methods of the present invention.

In another embodiment, this invention provides a method of preparing a maleate salt of a compound of Formula I:

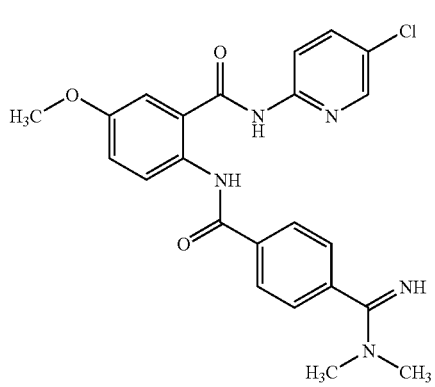

comprising contacting the compound of Formula I with at least a molar equivalent of maleic acid in a solvent mixture of $C_{1-4}$ alkanol and water at a temperature of between 10° C. and 40° C. under reaction conditions to form the maleate salt of the compound of Formula I. The compound of Formula I is prepared by contacting $LiN(CH_3)_2$ with a compound of Formula F:

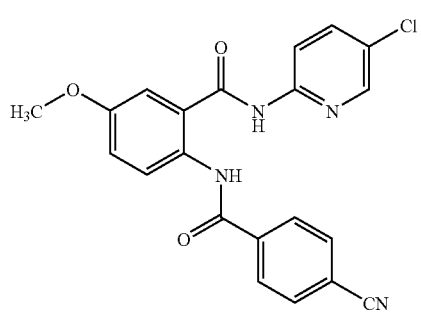

or a salt thereof, under reaction conditions to form the compound of Formula I. In a preferred embodiment, the salt of the compound of Formula F is a HCl salt. In another preferred embodiment, the reaction conditions comprise nucleophilic addition reaction conditions. In another embodiment, the reaction conditions comprise an aprotic solvent. In a preferred embodiment, the aprotic solvent is selected from the group consisting of tetrahydrofuran, diethyl ether, dimethoxymethane, dioxane, hexane, methyl tert-butyl ether, heptane, cyclohexane, and mixtures thereof. In another preferred embodiment, the aprotic solvent is tetrahydrofuran. In another embodiment, the reaction conditions comprise a temperature of less than or equal to 10° C. In another embodiment, the $LiN(CH_3)_2$ is prepared by contacting dimethylamine with an alkyllithium. As used herein, the term "alkyl" refers to a hydrocarbyl radical of from 1 to 8 carbon atoms. In another embodiment, the alkyllithium is n-butyllithium, tert-butyllithium, or hexyllithium. In a preferred embodiment, the alkyllithium is hexyllithium. In another embodiment, the compound of Formula I is afforded in a yield of at least 75%.

In another embodiment, this invention provides a method of preparing a maleate salt of a compound of Formula I:

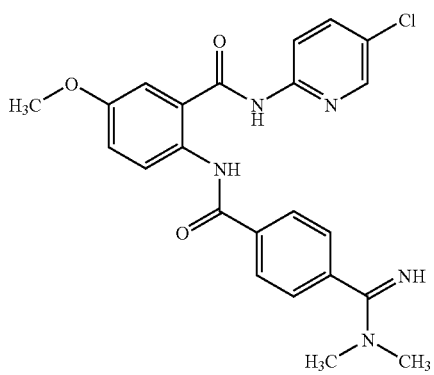

comprising contacting the compound of Formula I with at least a molar equivalent of maleic acid in a solvent mixture of $C_{1-4}$ alkanol and water at a temperature of between 10° C. and 40° C. under reaction conditions to form the maleate salt of the compound of Formula I. The compound of Formula I is prepared by contacting $LiN(CH_3)_2$ with a compound of Formula F:

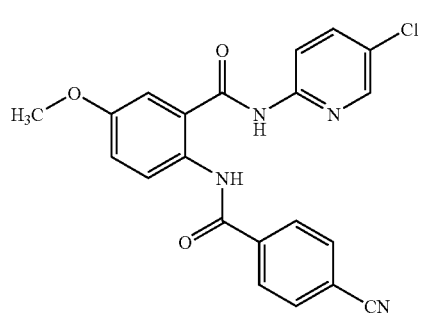

or a salt thereof, under reaction conditions to form the compound of Formula I. The compound of Formula F or a salt thereof is prepared by contacting a compound of Formula D:

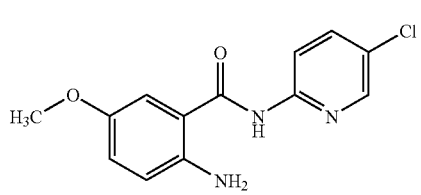

with a compound of Formula E:

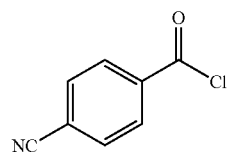

under reaction conditions to form the compound of Formula F or a salt thereof. In another embodiment, the reaction conditions comprise a solvent selected from the group consisting of tetrahydrofuran, diethyl ether, dimethoxymethane, dioxane, hexane, methyl tert-butyl ether, heptane, cyclohexane, and mixtures thereof. In a preferred embodiment, the reaction conditions comprise tetrahydrofuran as a solvent. In another embodiment, the method is performed between 19° C. and 30° C. In another embodiment, the compound of Formula F is afforded in a yield of at least 71%. In another embodiment, the compound of Formula F is afforded in a yield of at least 74%.

In another embodiment, this invention provides a method of preparing a maleate salt of a compound of Formula I:

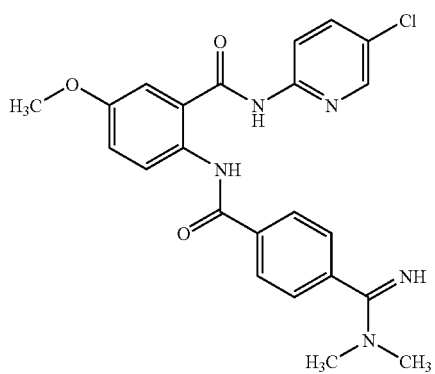

comprising contacting the compound of Formula I with at least a molar equivalent of maleic acid in a solvent mixture of $C_{1-4}$ alkanol and water at a temperature of between 10° C. and 40° C. under reaction conditions to form the maleate salt of the compound of Formula I. The compound of Formula I is prepared by contacting $LiN(CH_3)_2$ with a compound of Formula F:

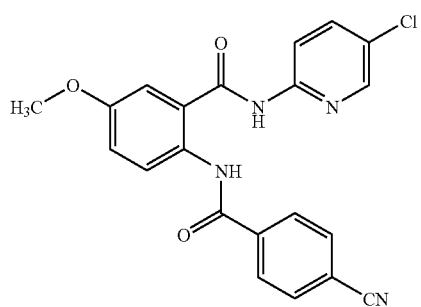

or a salt thereof, under reaction conditions to form the compound of Formula I. The compound of Formula F is prepared by contacting a compound of Formula D:

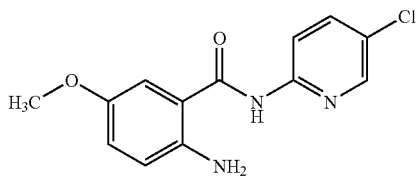

with a compound of Formula E:

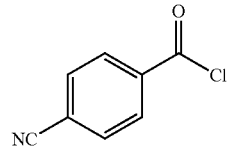

under reaction conditions to form the compound of Formula F or a salt thereof. The compound of Formula D is prepared by exposing a compound of Formula C:

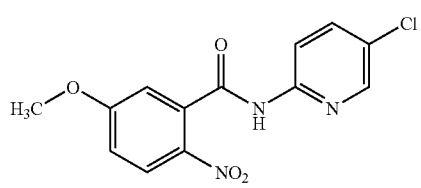

to reaction conditions to form the compound of Formula D. In another embodiment, the reaction conditions comprise hydrogen gas in the presence of a catalyst. In another embodiment, the catalyst is sulfided 5% platinum on carbon. In another embodiment, the reaction conditions comprise a temperature of between 19° C. and 28° C. and a pressure of hydrogen from 20 to 40 psi, preferably 30 psi. In one embodiment, the reaction conditions comprise a solvent selected from the group consisting of methylene chloride, ethanol, methanol, and ethyl acetate. In another embodiment, the conditions comprise methylene chloride as a solvent. In another embodiment, the compound of Formula D is afforded in a yield of at least 80%. In another embodiment, the compound of Formula D is afforded in a yield of at least 85%.

In another embodiment, this invention provides a method of preparing a maleate salt of a compound of Formula I:

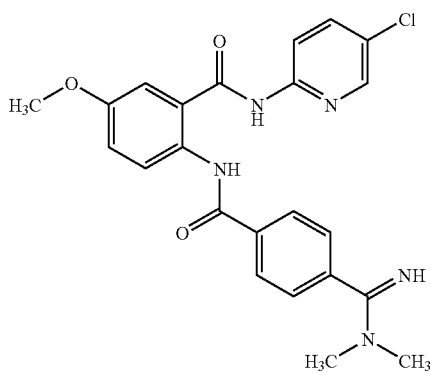

comprising contacting the compound of Formula I with at least a molar equivalent of maleic acid in a solvent mixture of $C_{1-4}$ alkanol and water at a temperature of between 10° C. and 40° C. under reaction conditions to form the maleate salt of the compound of Formula I. The compound of Formula I is prepared by contacting LiN(CH₃)₂ with a compound of Formula F:

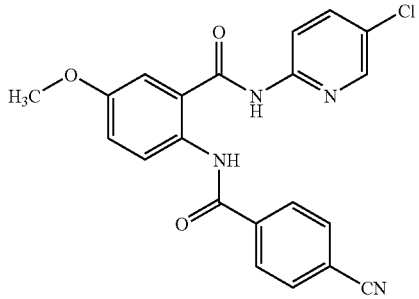

or a salt thereof, under reaction conditions to form the compound of Formula I. The compound of Formula F or a salt thereof is prepared by contacting a compound of Formula D:

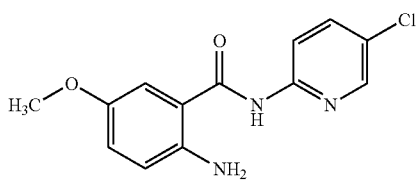

with a compound of Formula E:

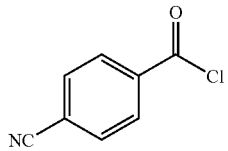

under reaction conditions to form the compound of Formula F or a salt thereof. The compound of Formula D is prepared by exposing a compound of Formula C:

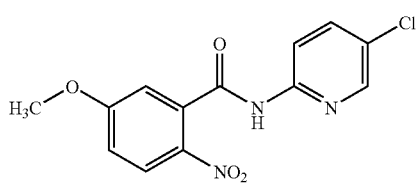

to reaction conditions to form the compound of Formula D, wherein the compound of Formula C is prepared by contacting a compound of Formula A:

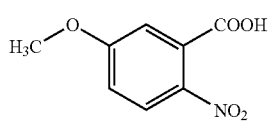

with a compound of Formula B:

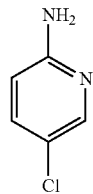

under reaction conditions to form the compound of Formula C. In another embodiment, the reaction conditions comprise a temperature of between 19° C. to 28° C. In another embodiment, the reaction conditions comprise acetonitrile as a solvent. In another embodiment, the reaction conditions may further contain other aprotic solvents in a small quantity. In one embodiment, the reaction conditions comprise phosphorous oxychloride and pyridine. In a preferred embodiment, the reaction conditions comprise about 1 to 1.9 equivalents of phosphorous oxychloride, wherein the equivalents are based on the compound of Formula A. In a preferred embodiment, the amount of phosphorous oxychloride in is less than 1.5 equivalents. In another preferred embodiment, the amount of phosphorous oxychloride is 1.2 equivalents. In another embodiment, the compound of Formula C is afforded in a yield of at least 84%. In another embodiment, the compound of Formula C is afforded in a yield of at least 88%.

In another embodiment, this invention provides a method of preparing a maleate salt of a compound of Formula I:

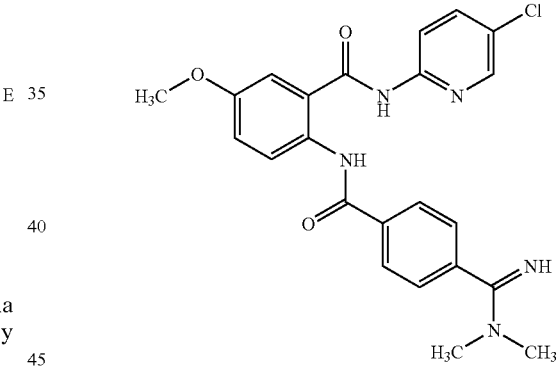

comprising:
a) contacting a compound of Formula A:

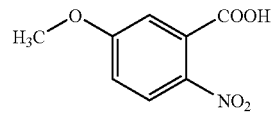

with a compound of Formula B:

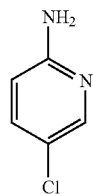

under reaction conditions to form a compound of Formula C:

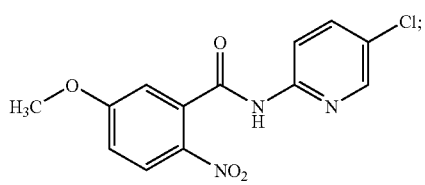

b) exposing the compound of Formula C to reaction conditions to form a compound of Formula D:

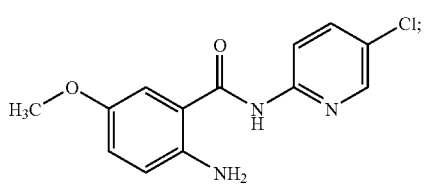

c) contacting the compound of Formula D with a compound of Formula E:

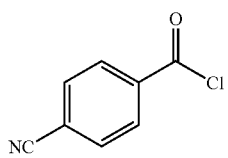

under reaction conditions to form a compound of Formula F:

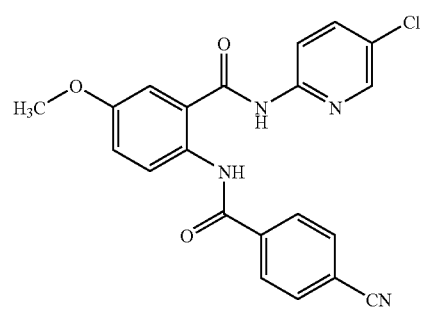

or a salt thereof;

d) contacting LiN(CH$_3$)$_2$ with the compound of Formula F or a salt thereof, under reaction conditions to form the compound of Formula I; and e) contacting the compound of Formula I with at least a molar equivalent of maleic acid in a solvent mixture of C$_{1-4}$ alkanol and water at a temperature of between 10° C. and 40° C. under reaction conditions to form the maleate salt of the compound of Formula I.

In another embodiment, this invention provides a method of preparing a maleate salt of a compound of Formula I on a kilogram scale.

In another embodiment, this invention provides a method of preparing a compound

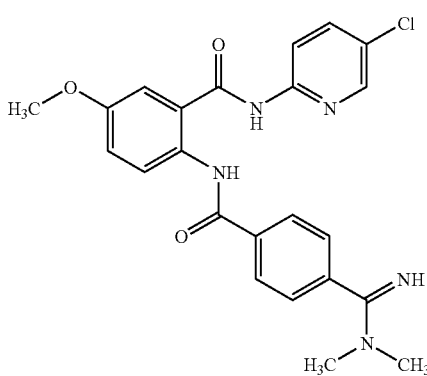

comprising:

a) contacting a compound of Formula A:

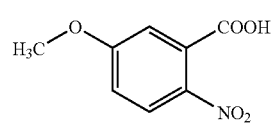

with a compound of Formula B:

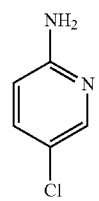

under reaction conditions comprising acetonitrile as a solvent to form a compound of Formula C:

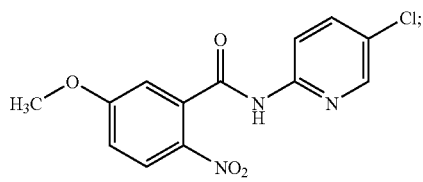

b) exposing the compound of Formula C to reaction conditions to form a compound of Formula D:

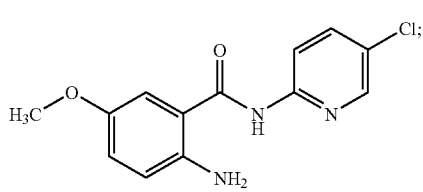

c) contacting the compound of Formula D with a compound of Formula E:

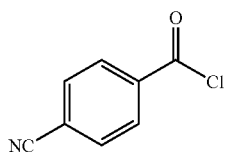

E under reaction conditions to form a compound of Formula F:

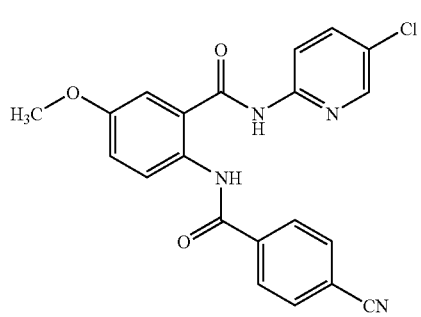

F or a salt thereof; and
d) contacting LiN(CH$_3$)$_2$ with the compound of Formula F or a salt thereof, under reaction conditions to form the compound of Formula I.

In another embodiment, this invention provides a method of preparing a compound of Formula I from a compound of Formula A on a kilogram scale.

In another embodiment, this invention provides a method of preparing a compound of Formula C:

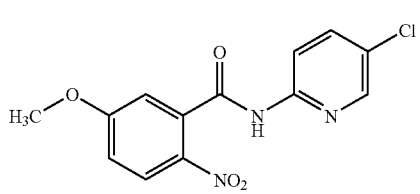

C by contacting a compound of Formula A:

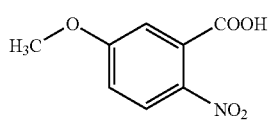

A with a compound of Formula B:

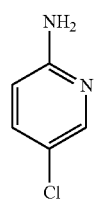

B under reaction conditions comprising acetonitrile as a solvent to form the compound of Formula C. In another embodiment, the reaction conditions comprise a temperature of between 19° C. to 28° C. In another embodiment, the reaction conditions further comprise phosphorous oxychloride and pyridine. In a preferred embodiment, the reaction conditions comprise about 1 to 1.9 equivalents of phosphorous oxychloride, wherein the equivalents are based on the compound of Formula A. In a preferred embodiment, the amount of phosphorous oxychloride in is less than 1.5 equivalents. In another preferred embodiment, the amount of phosphorous oxychloride is 1.2 equivalents. In another embodiment, the compound of Formula C is afforded in a yield of at least 84%. In another embodiment, the compound of Formula C is afforded in a yield of at least 88%.

In another embodiment, this invention provides a method of preparing a compound of Formula C from a compound of Formula A on a kilogram scale.

In another embodiment, this invention provides a method of preparing a compound of Formula D:

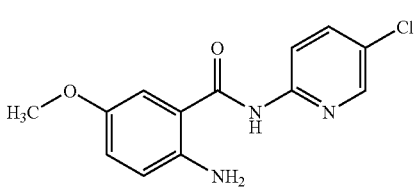

D by exposing a compound of Formula C:

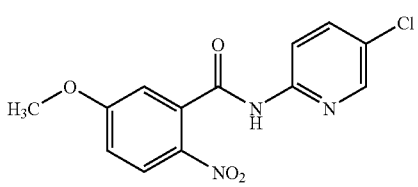

C to reaction conditions to form the compound of Formula D. In another embodiment, the reaction conditions comprise hydrogen gas in the presence of a catalyst. In another embodiment, the catalyst is sulfided 5% platinum on carbon. In another embodiment, the reaction conditions comprise a temperature of between 19° C. and 28° C. and a pressure of hydrogen from 20 to 40 psi, preferably 30 psi. In one embodiment, the reaction conditions comprise a solvent selected from the group consisting of methylene chloride, ethanol, methanol, and ethyl acetate. In another embodiment, the conditions comprise methylene chloride as a solvent. In, another embodiment, the compound of Formula D is afforded in a yield of at least 80%. In another embodiment, the compound of Formula D is afforded in a yield of at least 85%.

In another embodiment, this invention provides a method of preparing a compound of Formula D from a compound of Formula C on a kilogram scale.

In another embodiment, this invention provides a method of preparing a compound of Formula D:

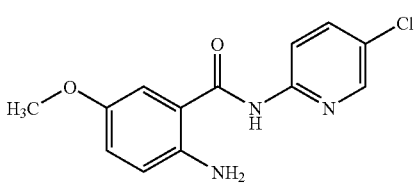

D comprising:
a) contacting a compound of Formula A:

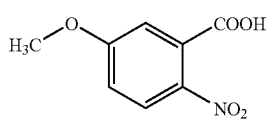

A with a compound of Formula B:

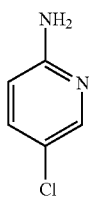
B under reaction conditions comprising acetonitrile as a solvent to form a compound of Formula C:

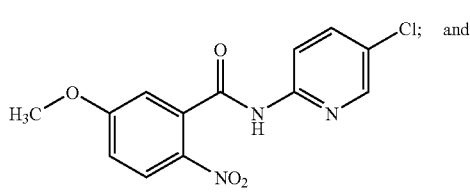
C; and b) exposing the compound of Formula C to reaction conditions to form the compound of Formula D.

In another embodiment, this invention provides a method of preparing a compound of Formula D from a compound of Formula A on a kilogram scale.

In another embodiment, this invention provides a method of preparing a compound of Formula F:

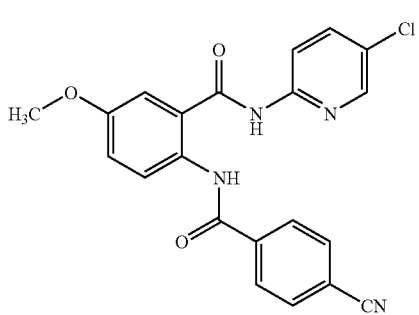
F or a salt thereof, by contacting a compound of Formula D:

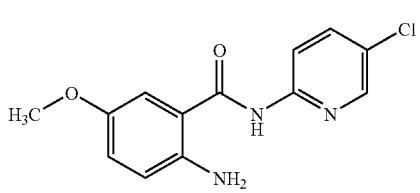
D with a compound of Formula E:

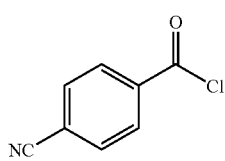
E under reaction conditions to form the compound of Formula F or a salt thereof. In another embodiment, the reaction conditions comprise a solvent selected from the group consisting of tetrahydrofuran, diethyl ether, dimethoxymethane, dioxane, hexane, methyl tert-butyl ether, heptane, cyclohexane and mixtures thereof. In a preferred embodiment, the reaction conditions comprise tetrahydrofuran as a solvent. In another embodiment, the method is performed between 19° C. and 30° C. In another embodiment, the compound of Formula F is afforded in a yield of at least 71%. In another embodiment, the compound of Formula F is afforded in a yield of at least 74%.

In another embodiment, this invention provides a method of preparing a compound of Formula F from a compound of Formula D on a kilogram scale.

In another embodiment, this invention provides a method of preparing a compound of Formula F or a salt thereof:

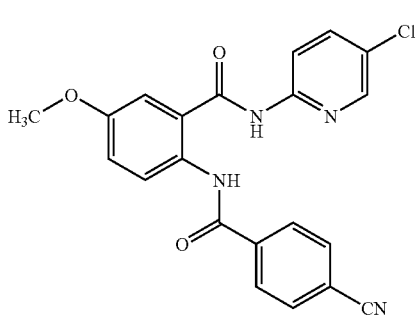
F comprising:
a) contacting a compound of Formula A:

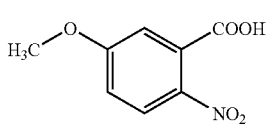
A with a compound of Formula B:

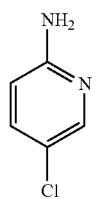
B under reaction conditions comprising acetonitrile as a solvent to form a compound of Formula C:

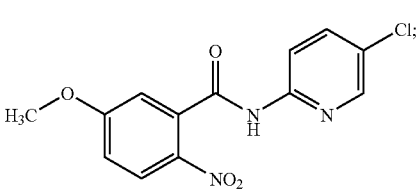
C b) exposing the compound of Formula C to reaction conditions to form a compound of Formula D:

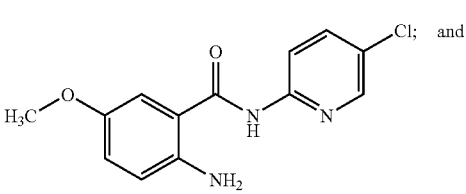
D; and c) contacting the compound of Formula D with a compound of Formula E:

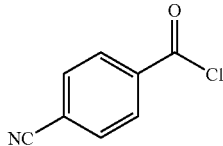

under reaction conditions to form a compound of Formula F or a salt thereof.

In another embodiment, this invention provides a method of preparing a compound of Formula F or a salt thereof from a compound of Formula A on a kilogram scale.

In another embodiment, this invention provides a method of preparing a compound of Formula I:

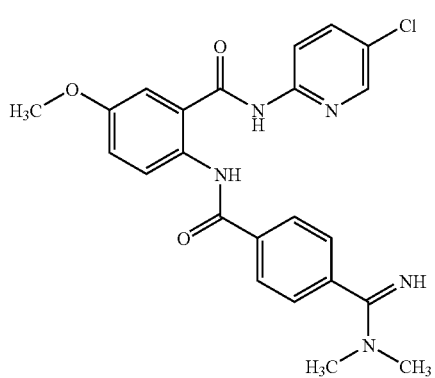

by contacting LiN(CH$_3$)$_2$ with a compound of Formula F:

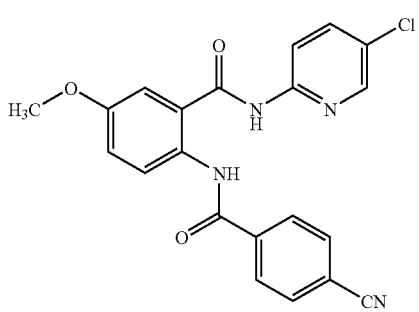

or a salt thereof, under reaction conditions to form the compound of Formula I. In a preferred embodiment, the reaction conditions comprise nucleophilic addition reaction conditions. In another embodiment, the reaction conditions comprise an aprotic solvent. In a preferred embodiment, the aprotic solvent is selected from the group consisting of tetrahydrofuran, diethyl ether, dimethoxymethane, dioxane, hexane, methyl tert-butyl ether, heptane, cyclohexane, and mixtures thereof. In another preferred embodiment, the aprotic solvent is tetrahydrofuran. In another embodiment, the reaction conditions comprise a temperature of less than 10° C. In another embodiment, the LiN(CH$_3$)$_2$ is prepared by contacting dimethylamine with alkyllithium. In another embodiment, the alkyllithium is n-butyllithium, tert-butyllithium, or hexyllithium. In a preferred embodiment, the alkyllithium is hexyllithium. In another embodiment, the compound of Formula I is afforded in a yield of at least 75%.

In another embodiment, this invention provides a method of preparing a compound of Formula I from a compound of Formula F or a salt thereof on a kilogram scale.

B. Synthesis of the Compound of Formula I

A synthesis of the compound of Formula I starting with a compound of Formula A is reported in U.S. Pat. No. 6,844,367 (the '367 patent). The current invention provides an improved synthesis, wherein the improvements employ milder conditions and/or higher yields. Milder conditions include lower temperatures, less amount of reagents or by-products, etc.

The following Tables compare the procedures to prepare the compound of Formula I and the intermediates as described in the '367 patent with the process of the present invention. Please note that the exact conditions and yields listed in Tables 1-3 are taken from Example 259 of the '367 patent, which describes a procedure for preparing N-{2-[N-(5-bromo(2-pyridyl))carbamoyl]-4,5-dimethoxyphenyl}4-cyanophenyl)carboxamide, a compound similar to the compound of Formula F. Example 262 of the '367 patent recites that the compound of Formula F was prepared according to the procedure described in Example 259.

Part a) Preparation of a Compound of Formula C

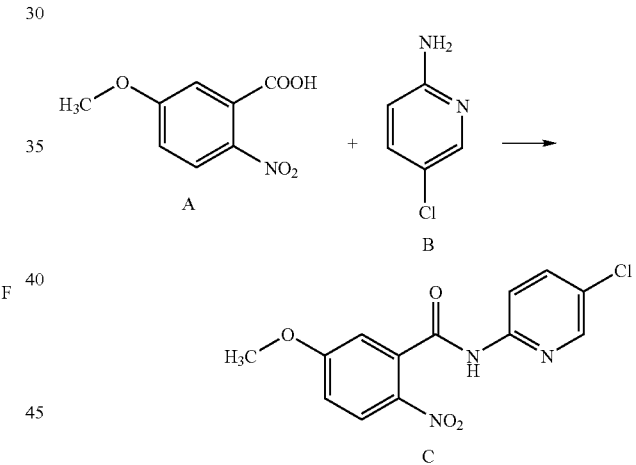

TABLE 1

| Reaction conditions | U.S. Pat. No. 6,844,367 | Current Protocol |
| --- | --- | --- |
| Amount of A | 10 mmol (1 eq.) | 25 kg (1 eq.) |
| Amount of B | 14 mmol (1.4 eq.) | 16.3 kg (1 eq.) |
| Solvent | anhydrous pyridine (50 mL) | anhydrous pyridine (30 kg, 3 eq.) |
| POCl$_3$ | 20 mmol (2 eq.) | 23.3 kg, (1.2 eq.) |
| Another solvent | — | acetonitrile (87.5 kg) |
| Temperature | 0° C. to RT | 19° C. to 28° C. |
| Time | 0.5 hr | 1 hr |
| Yield | 80% | 88.2% |

Preparation of the compound of Formula C involves coupling of the carboxylic acid in the compound of Formula A with the primary amine in the compound of Formula B. This coupling is carried out by converting the carboxylic acid into its acid chloride using phosphorous oxychloride. As shown in the Table 1, the '367 patent uses 1.4 equivalents of the compound of Formula B and 2 equivalents of phosphorous oxychloride whereas the current protocol uses 1 equivalent of the compound of Formula B and 1.2 equivalents of phosphorous oxychloride. In addition, in the current protocol the solvent comprises a mixture of acetonitrile and pyridine. This significantly reduced the amount of the toxic and corrosive phosphorous oxychloride and pyridine. Reducing the ratio of the amino starting material to the acid starting material from 1.4:1 to 1:1 also eliminated the need to remove a large amount of access starting material, simplifying the isolation process. As evidenced above, the current milder reaction conditions give significant improvement in yield, 88.2% versus 80% reported in the '367 patent.

Part b) Preparation of a Compound of Formula D

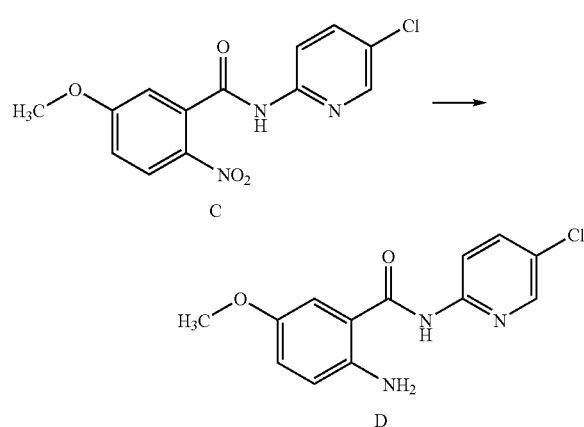

TABLE 2

| Reaction conditions | U.S. Pat. No. 6,844,367 | Current Protocol |
| --- | --- | --- |
| Amount of C | 0.83 mmol (1 eq.) | 33 kg (1 eq.) |
| Reducing agent | SnCl$_2$•2H$_2$O (4 mmol, 4.8 eq.) | H$_2$, 5% Pt/C (sulfided, 0.33 kg) |
| Solvent | EtOAc (10 mL) | CH$_2$Cl$_2$ (578 kg) |
| Temperature | reflux | 19° C. to 31° C. |
| Time | 1 hr | 30-60 hr |
| Yield | 78% | 89.5% |

Preparation of the compound of Formula D involves reduction of the nitro group in the compound of Formula C. As shown in the Table 2, the '367 patent uses 4.8 equivalents of SnCl$_2$.2H$_2$O as the reducing agent. The use of SnCl$_2$.2H$_2$O (note that at least 4.0 eq. of SnCl$_2$.2H$_2$O is required to complete this reduction) produces of a large amount of SnCl$_4$ by-product, which can be very difficult to remove from the reaction mixture and often causes a significant problem in isolating the desired product Formula D. The current protocol uses hydrogenation with hydrogen gas with 1 wt % (wherein wt % is based on the amount of compound of Formula C) of sulfided 5% Pt/C as a catalyst. The limited amount of catalyst can be readily removed by filtration through a celite bed, leaving only the product in a solvent. This significantly simplifies the isolation process, especially for large scale, such as hundred-gram scale or kilogram scale, preparations. Also, the '367 patent uses ethyl acetate as a solvent and the reaction is carried out at reflux temperature (77° C.) while the current protocol uses methylene chloride as a solvent and the reaction is carried out at 19-28° C. Thus, the current protocol, notwithstanding the use of milder reaction conditions, gives significant improvement in yield, 89.5% versus 78% reported in the '367 patent.

Part c) Preparation of a Compound of Formula F

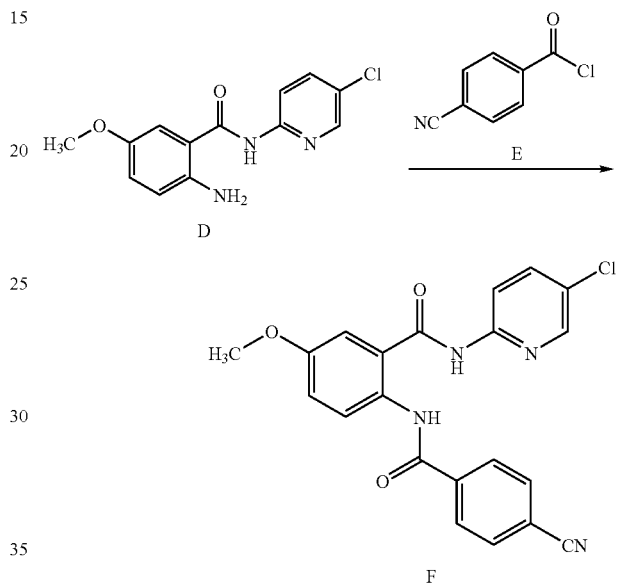

TABLE 3

| Reaction conditions | U.S. Pat. No. 6,844,367 | Current Protocol |
| --- | --- | --- |
| Amount of D | 0.57 mmol (1 eq.) | 26.4 kg (1 eq.) |
| Amount of E | 0.85 mmol (1.5 eq.) | 17.2 kg (1.1 eq.) |
| Solvent | CH$_2$Cl$_2$ (10 mL) | THF (548 kg) |
| Pyridine | 3 mL | 2.9 kg |
| Temperature | RT | 19° C. to 30° C. |
| Time | immediate | 2 hr |
| Product | F | HCl salt of F |
| Yield | 70% | 74.8% |

Preparation the compound of Formula F involves coupling of the primary amine in the compound of Formula D with the acid chloride in the compound of Formula E. As shown in the Table 3, U.S. Pat. No. 6,844,367 uses 1.5 equivalents of the compound of Formula E while the current protocol uses 1.1. equivalents of the compound of Formula E. The '367 patent uses methylene chloride as a solvent while the current protocol uses tetrahydrofuran as a solvent. Thus, the current protocol uses less amount of the compound of Formula E and gives an improvement in yield, 74.8% versus 70% reported in the '367 patent.

Part d) Preparation of a Compound of Formula I

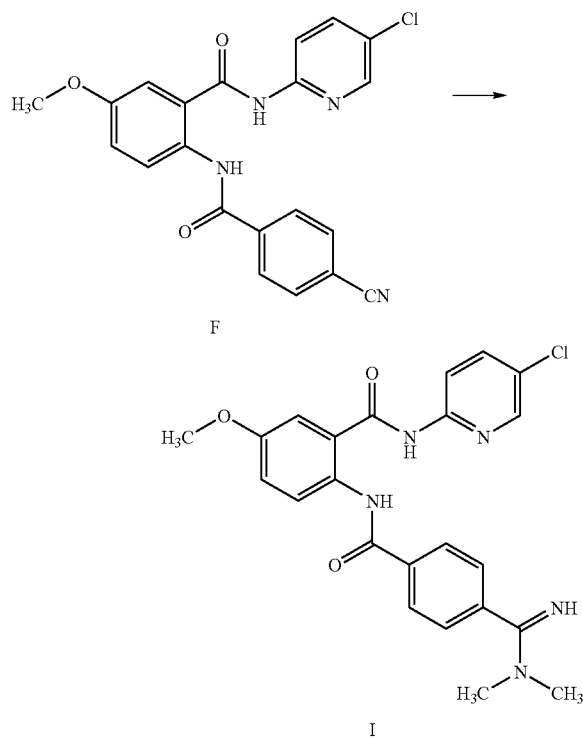

TABLE 4

(Conditions listed under the '367 patent are taken from Example 263 which describes a preparation for a similar compound, N-(5-chloro(2-pyridyl))-(5-methoxy-2-{[4-(1-methyl-2-imidazolin-2-yl))phenyl]-carbonylamino}phenyl)carboxamide.

| Reaction conditions | U.S. Pat. No. 6,844,367 | Current Protocol |
|---|---|---|
| Amount of F | 100 mg converted to HCl salt of methoxy imidate intermediate in MeOH (5 mL) and EtOAC (5 mL) at 0° C. by passing HCl gas | 31.5 kg (1 eq.) as HCl salt |
| Amount of dimethyl amine | 0.76 mL | 161 kg (5 eq.), 2M in THF |
| Solvent | Anhydrous MeOH (10 mL) | THF (349 kg) |
| Hexyllithium | — | 97.2 kg (4.5 eq, 2.3 M) |
| Temperature | reflux | −3° C. to 10° C. |
| Time | 1 hr | 1 hr |
| Yield | — | 76.7% |

Example 266 of the '367 patent recites that the compound of Formula I was prepared according to the procedure described in Example 263.)

Preparation of the compound of formula I involves conversion of nitrile in the compound of Formula F to the amidino group. As shown in Table 4, the '367 patent uses a two-step method wherein the nitrile in the compound of Formula F is first converted to the methoxy imidate intermediate via reaction with methanol and the highly corrosive HCl gas. This is followed by a second step of reaction with dimethyl amine in methanol under reflux (65° C.) to give the compound of Formula I. The current protocol uses a one-step method wherein the addition of the anion of dimethyl amine to the nitrile in the HCl salt of the compound of Formula F in tetrahydrofuran at −3° C. to 10° C. gives the compound of Formula I in 76.7% yield. Thus, the current protocol uses a one-step method with milder conditions.

C. Preventing and Treating Disease Conditions Characterized by Undesired Thrombosis The compound and/or salt prepared by the present invention can be used for preventing or treating a condition in a mammal characterized by undesired thrombosis by administering to the mammal a therapeutically effective amount of the maleate salt of the compound of Formula I. The maleate salt of the compound of Formula I can be used either alone or in conjunction with pharmaceutically acceptable excipients to prevent the onset of a condition characterized by undesired thrombosis. Prophylactic treatment can have substantial benefits for a patient at risk of an ailment, through decreased medical treatments and their associated mental and physical costs, as well as the direct monetary savings from avoiding prolonged treatment of a patient. For patients where the condition is not detected sufficiently early to prevent onset, the compound and/or salt of the present invention can be used either alone or in conjunction with pharmaceutically acceptable excipients to treat the condition.

The preferred compound and/or salt of the present invention is characterized by its ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The compounds of the present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Accordingly, a method for preventing or treating a condition in a mammal characterized by undesired thrombosis comprises administering to the mammal a therapeutically effective amount of a compound of this invention. Disease states that are treatable using the compounds of the present invention include, but are not limited to, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboanglitis obliterans, thrombotic disease associated with heparin-induced thrombocytopenia, thrombotic complications associated with extracorporeal circulation, thrombotic complications associated with instrumentation, thrombotic complications associated with the fitting of prosthetic devices, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

The maleate salt of the compound of Formula I can also be used whenever inhibition of blood coagulation is required such as to prevent coagulation of stored whole blood and to prevent coagulation in other biological samples for testing or storage. Thus coagulation inhibitors of the present inhibition can be added to or contacted with stored whole blood and any medium containing or suspected of containing plasma coagulation factors and in which it is desired that blood coagulation be inhibited, e.g. when contacting the mammal's blood with material selected from the group consisting of vascular grafts, stents, orthopedic prosthesis, cardiac prosthesis, and extracorporeal circulation systems.

Besides being useful for human treatment, these compounds are also useful for veterinary treatment of companion animals, exotic animals and farm animals, including mammals, rodents, and the like. More preferred animals include horses, dogs, and cats.

D. Administration

Therapeutic liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound and/or salt of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of the compounds are commenced at lower dosage levels, with dosage levels being increased until the desired effect is achieved.

Typical adjuvants which may be incorporated into tablets, capsules, lozenges and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

E. Combination Therapies

The compounds of the present invention may also be used in combination with other therapeutic or diagnostic agents. In certain preferred embodiments, the compounds of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of this invention can be utilized in vivo, ordinarily in mammals such as primates, humans, sheep, horses, cattle, pigs, dogs, cats, rats and mice, or in vitro.

IV. Examples

Unless stated otherwise, the abbreviations used throughout the specification have the following meanings:
A %=total percent area
aq.=aqueous
cm=centimeter
d=doublet
EDTA=ethylenediaminetetraacetic acid
eq. equivalent
EtOH=ethanol
g=gram
HPLC=high performance liquid chromatography
hr=hour
Hz=hertz
IR=infrared
J=coupling constant
kg=kilogram
L=liter
LOD=limit of detection
M=molar m=multiplet
Me=methyl
MeO=methoxy
MeOH=methanol
mg=milligram
min.=minute
mL=milliliter
mm=millimeter
MTBE=methyl tert butyl ether
N=Normal
nM=nanomolar
NMR=nuclear magnetic resonance
s=singlet
TDS=total dissolved solids
THF=tetrahydrofuran
μM=micromolar Example 1

Preparation of a Maleate Salt of a Compound of Formula I

Gram Scale Preparation

In a 3-necked 1500 mL round bottomed flash equipped with a condenser, free base compound of Formula I (25 g; 1 eq.) was charged and 9:1 EtOH/Water (500 mL) was added while stirring. The resulting slurry was heated to 70° C. Maleic acid (12.77 g; 2 eq.) was added dropwise as a solution (100 mL of 9:1 EtOH/Water) and after 50 mL had been added, the solution became noticeably clearer. On complete addition of the maleic acid solution the temperature was held at 80° C. for 5 minutes. The vessel was allowed to cool slowly to 45° C. and 400 mL of MTBE was then added. The solution was stirred for another 12 hr. The resulting precipitate was filtered and dried under vacuum. The maleate salt of the compound of Formula I was recovered in a 45% yield (14.2 g).

Kilogram Scale Preparation

The compound of Formula I (24.6 kg) was charged into a 760 L GLMS reactor (Reactor A). Maleic acid (12.7 kg, 2.0 eq), ethanol (445 kg, 18.1 parts), and high purity water (140 kg, 5.7 parts) were added. The reaction mixture was adjusted to 22° C. (19-25° C.) and agitated at that temperature for ca. 1 hr, then transferred through a polishing filter into a conditioned 780 L Hastelloy reactor (Reactor B). The Reactor A pump and lines were rinsed forward into Reactor B with additional ethanol (ca. 45 kg) via polishing filter. The filtrate was concentrated under vacuum with a maximum temperature of warm glycol bath (to heat reactor jacket) of 45° C., until ca. 140 L (5.7 parts volume) remained. The Reactor B contents were sampled for in-process NMR, which showed that the mole ratio of ethanol:the maleate salt of the compound of Formula I was 26. High purity water (49 kg, 2.0 parts) was charged to Reactor B and concentration under vacuum resumed until a pot volume of ca. 140 L (5.7 parts volume) was achieved. In-process NMR indicated that the mole ratio of ethanol:the maleate salt of the compound of Formula I was 14. High purity water (49 kg, 2.0 parts) was again charged and concentration under vacuum resumed to obtain a pot volume of ca. 140 L. In-process NMR showed that the mole ratio of ethanol:the maleate salt of the compound of Formula I was 5. The temperature of the Reactor B contents were adjusted to 22° C. (19-25° C.) and formation of a slurry was visually confirmed. The reaction mixture was agitated at 22° C. (19-25° C.) for ca. 2 hrs, and then filtered onto a 30" centrifuge fitted with a filter cloth. The Reactor B pump and lines were rinsed forward to the 30" centrifuge via polishing filter with two portions of high purity water (ca. 30 kg each). The filter cake was sampled for in-process HPLC, which showed that the purity of the product was 99.1 A %, the largest impurity was 0.26 A %, and therefore recrystallization was unnecessary. The filter cake (33.1 kg) was dried under vacuum with a maximum temperature of warm glycol bath (to heat dryer jacket) of 40° C. After ca. 30.5 hrs, in-process LOD analysis indicated a solvent content of 0%. The dry product was discharged (26.4 kg) and stored at 2-8° C. The yield for the final product was slightly higher than expected at 85% (expected 50-80%). Purity of the maleate salt was measured by the presence of hydrolyzed amidine content as measured by HPLC, and the purity was found to be >99%.

$^1$H NMR (DMSO-d$_6$): δ 3.0 (s, 3H), 3.2 (s, 3H), 3.82 (s, 3H), 7.2 (d, 1H, J=9.0 Hz), 7.42 (s, 1H), 7.68 (d, 1H, J=8.0 Hz), 7.95-8.15 (m, 2H), 8.12 (m), 8.18 (m, 1H), 8.42 (s, 1H), 9.0 (s, 1H), 11.0 (s, 1H), 11.2 (s, 1H); IR (KBr, cm$^{-1}$): 3300, 1685, 1600, 1515, 1380, 1270, 1200, 1100, 1050, 880, 800, 710.

Example 2

Preparation of the Compound of Formula I

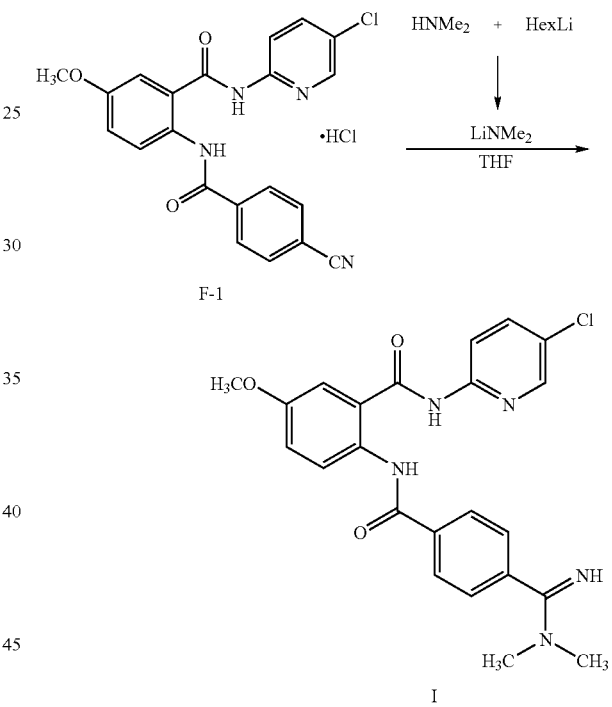

Gram Scale Preparation

A slurry of the compound of Formula F-1 (455 g, 1.0 eq.) in THF (4.67 kg, 10.3 parts) was prepared and adjusted to <10° C. Lithium dimethyl amide was prepared as follows: hexyllithium (2.3 N/hexane, 2.45 L, 5.5 eq.) was added to dimethylamine solution (2 N/THF, 2.8 L, 5.5 eq.) maintaining <10° C. The lithium dimethyl amide solution was charged into the slurry containing the compound of Formula F-1 keeping the pot temperature of <10° C. The reaction progress was monitored by in-process HPLC which confirmed that the amount of Formula F-1 was <1.0 A %. A buffer solution of NaHCO$_3$ (490 g, 1.1 parts, 5.7 eq.) and Na$_2$CO$_3$ (490 g, 1.1 parts, 4.5 eq.) in deionized water (6.6 kg, 14.51 parts) was prepared, and the above reaction mixture was transferred to this aqueous solution maintaining <5° C. The product precipitated out and the resulting slurry was adjusted to 20° C. over a period of 12 hr. The solid was filtered, and the resulting wet cake was washed with 3.5 kg (7.7 parts) of deionized water. The solid was filtered off using a coarse frit glass bench filter, and rinsed forwarded with cold (0-5° C.) absolute ethanol (628 g, 1.4 parts). The product was dried at 30-35° C. Dry product was obtained in 458 g (73% yield).

Kilogram Scale Preparation

A slurry of the compound of Formula F-1 (31.5 kg, 1.0 eq.) in THF (251 kg, 8.0 parts) was prepared in a 780 L Hastelloy reactor (Reactor A) and adjusted to 0° C. (−3 to 3° C.). 2 M Dimethylamine in THF (161.0 kg, 5.0 eq.) and THF (63 kg, 2 parts) were charged into a 1900 L GLMS reactor (Reactor B) and adjusted to 0° C. (−3 to 3° C.) with maximum agitation. Hexyllithium (2.3 M, 97.2 kg, 4.5 eq.) was slowly charged to Reactor B while maintaining a max temperature of 10° C. The pump and lines were rinsed forward to Reactor B with THF (3.2 kg). The Reactor B contents were adjusted to 0° C. (−3 to 3° C.), then transferred to Reactor A while keeping Reactor A temperature ≦10° C. The Reactor B pump and lines were rinsed forward with THF (31.4 kg, 1.0 part). The Reactor A contents were adjusted to 0° C. (−3 to 3° C.), and agitated at this temperature until the reaction was complete as verified by HPLC (1-2 hrs). After about 1 hr of agitation, in-process HPLC analysis indicated that 0 A % starting material remained (in-process criteria: max 1 A %). Reactor A contents were adjusted to −5° C. (−8 to −3° C.). In-process cleaning of Reactor B with water was performed. Two previously prepared aqueous solutions [NaHCO₃ (35.0 kg, 1.1 parts) in water (236 kg, 7.5 parts), and Na₂CO₃ (35.0 kg 1.1 parts) in water (236 kg, 7.5 parts)] were charged to Reactor B and adjusted to −3° C. (0 to 6° C.). Reactor A contents were transferred to Reactor B through an insulated line, maintaining the temperature of Reactor B at −8° C. to a maximum of 5° C. The Reactor A pump and lines were rinsed forward with cold [−5° C. (−8 to −3° C.)] THF (31.4 kg, 1.0 part). Reactor B contents were adjusted to 22° C. (19-25° C.) and agitated for ca. 3 hrs. Slurry formation was visually confirmed, and Reactor B contents were filtered onto a 30" centrifuge fitted with a filter cloth. The Reactor B pump and lines were rinsed forward onto the 30" centrifuge fitted with a filter cloth with drinking water (63 kg, 2 parts). The wet filter cake (66.5 kg) was transferred back to Reactor B and submitted to a slurry wash in drinking water (1005 kg, 32 parts) at 22° C. (19-25)° C. for ca. 1 hr. The product was filtered onto the 30" centrifuge (after in-process cleaning and fitting with a filter cloth), and the Reactor B lines and pump were rinsed forward with drinking water (63 kg, 2 parts). The water rinse was sampled for test by TDS, which was found to be 0.46%. The Reactor B pump, lines and wet filter cake were further rinsed with cold [0° C. (−3 to 3° C.)]ethanol (44 kg, 1.39 parts). The wet filter cake was dried under vacuum with a maximum temperature of water bath (to heat dryer jacket) of 35° C. In-process LOD was 0% after ca. 24 hrs of drying, and the product was discharged (24.8 kg) in 76.7% yield. HPLC showed 98% purity, with dechlorinated impurity at 1.14%.

Example 3

Preparation of the Compound of Formula F-1

Step 1. Synthesis of 2-nitro-N-(5-chloro-pyridin-2-yl)-5-methoxy-benzamide (C)

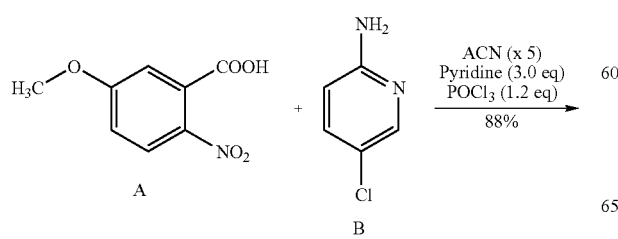

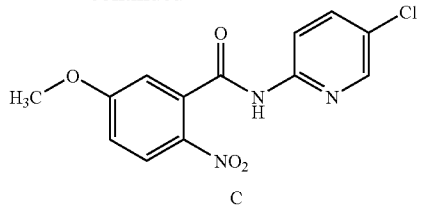

5-Methoxy-2-nitrobenzoic acid (A) (25.0 kg, 1.0 eq.), 2-amino-5-chloropyridine (B) (16.3 kg, 1.0 eq.), and acetonitrile (87.5 kg, 3.5 parts) were charged to a 380 L GLMS reactor. The reaction mixture was adjusted to 22° C. (19-25° C.) and anhydrous pyridine (30.0 kg, 3.0 eq.) was added. The pump and lines were rinsed forward with acetonitrile (22.5 kg, 0.9 parts), and the reactor contents were adjusted to a temperature of 19-22° C. Phosphorous oxychloride (23.3 kg, 1.20 eq.) was charged to the contents of the reactor via a metering pump, while maintaining a temperature of 25° C. (22-28° C.). The metering pump and lines were rinsed forward with acetonitrile (12.5 kg, 0.5 parts), while keeping the temperature at 25° C. (22-28° C.). The reaction mixture normally turned from a slurry to a clear solution after the addition of about ⅓ of the POCl₃. At the end of the addition, it became turbid. After complete addition, the reaction mixture was agitated at 25° C. (22-28° C.) for ca. 1 hr, at which time HPLC analysis confirmed reaction completion. The solution was cooled to 15° C. (12-18° C.) and drinking water (156.3 kg, 6.25 parts) was charged slowly while keeping reaction temperature of between 12 and 30° C. The reaction mixture was then adjusted to 22° C. (19-25° C.) and agitated for ca. 5 hrs until exotherm ceased. Formation of a slurry was visually confirmed and the contents of the reactor were filtered onto a pressure nutsche fitted with a filter cloth. The reactor, pump, and lines were washed forward onto the pressure nutsche with two portions of drinking water (62.5 kg, 2.5 parts each). The filtrate had a pH value of 7. The product (41.8 kg) was dried under vacuum with a maximum temperature of water bath (to heat dryer jacket) of 50° C. After ca. 12 hrs, in-process LOD analysis indicated a solvent content of 0.72%. The dry product (C) was discharged (34.4 kg) with 88.2% yield and 99.1% purity by HPLC.

Step 2. Synthesis of 2-amino-N-(5-chloro-pyridin-2-yl)-5-methoxy-benzamide (D)

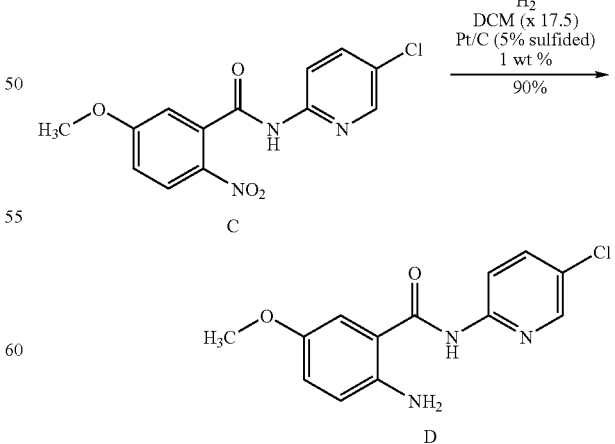

To a 780 L Hastelloy reactor, compound C (33 kg, 1.0 eq.), 5% platinum carbon (sulfided, 0.33 kg, 0.010 parts) and dichloromethane (578 kg, 17.5 parts) were charged. Agitation was started and reactor contents were adjusted to 22° C. (19-25° C.). The reactor was pressurized with ca. 30 psi hydrogen and the reaction mixture gently heated to 28° C. (25-31° C.). Hydrogenation of the reactor contents was performed under ca. 30 psi at 28° C. (25 to 31° C.; maximum 31° C.) until the reaction was complete by HPLC. After 16.5 hrs, the reaction was deemed complete after confirming the disappearance of starting material (0.472 A %). The contents of the reactor were circulated through a conditioned celite pad (0.2-0.5 kg celite conditioned with 20-55 kg dichloromethane) prepared in a 8" sparkler filter to remove the platinum catalyst. The reactor and celite bed were rinsed forward with two portions of dichloromethane (83 kg, 2.5 parts each). The filtrate was transferred to and concentrated in a 570 L GLMS reactor under a atmospheric pressure to ca. 132 L (4 parts volume). Ethanol (69 kg, 2.1 parts) was charged and concentration continued under atmospheric pressure to ca. 99 L (3 parts volume). In-process NMR indicated that the dichloromethane content was 39%. Ethanol (69 kg, 2.1 parts) was charged again and concentration continued again to ca. 99 L (3 parts volume). In-process NMR indicated that the dichloromethane content was 5%. The reaction mixture was then adjusted to 3° C. (0 to 6° C.), agitated for ca. 1 hr, and the resulting slurry filtered onto a jacketed pressure nutsche fitted with a filter cloth. The reactor, pump, and lines were rinsed forward with cold [3° C. (0-6° C.)]ethanol (26 kg, 0.8 parts). The wet filter cake (36.6 kg) was dried under vacuum at 40-50° C. with a maximum temperature of water bath (to heat dryer jacket) of 50° C. LOD analysis after 12.5 hrs indicated solvent content was at 0.1%. The dry product (D) was discharged (26.4 kg) in 89.5% yield. HPLC showed 98.4 A % purity, with dechlorinated impurity at 0.083%.

Step 3. Synthesis of N-(5-chloro-pyridin-2-yl)-2-(4-cyano-benzoyl-amino)-5-methoxy-benzamide hydrochloride (F-1)

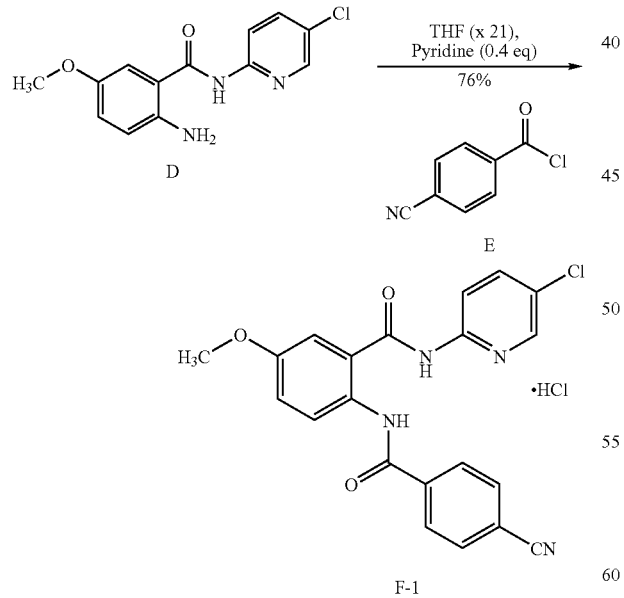

To a 780 L Hastelloy reactor, was charged 4-cyanobenzoyl chloride (E) (17.2 kg, 1.1 eq.) and THF (92 kg, 3.5 parts). Reactor contents were agitated at 22° C. (19-25° C.) until all of the solids had dissolved. The resulting solution was transferred to a lower receiver and the reactor was rinsed forward with THF (26 kg, 1 part). Compound D (26.4 kg, 1 eq.), THF (396 kg, 15 parts) and pyridine (2.90 kg, 0.4 eq.) were charged to a clean reactor. The pump and lines were rinsed forward with THF (34 kg, 1.3 parts). Via a metering pump, the 4-cyanobenzoyl chloride/THF solution was charged to the reactor, keeping the temperature at <30° C. and rinsing forward with THF (ca. 10 kg). The resulting yellow-colored slurry was agitated at 22° C. (19-25° C.) for ca 2 hrs. In-process HPLC taken after 2 hrs showed a compound of Formula D content of 0%, indicating completion of the reaction. The slurry was filtered onto a pressure nutsche fitted with a filter cloth. The reactor, pump, lines and wet cake were rinsed with three portions of ethanol (ca. 15 kg each). The wet filter cake was discharged (65.4 kg) and transferred back to the reactor for slurry wash in ethanol (317 kg, 12 parts) at 22° C. (19-25° C.) for ca. 1 hr. The slurry was filtered onto the pressure nutsche and the reactor, pump, lines, and wet filter cake were rinsed with two portions of ethanol (ca. 15 kg each) and two portions of THF (ca. 15 kg each). The wet filter cake was dried under vacuum with a maximum temperature of warm glycol bath (to heat the dryer jacket) of 40° C. After 14.5 hrs of drying, LOD was 0.75%. The dried material was milled (screen 0.125") to give 31.8 kg of product, which was dried under vacuum for another 10.5 hrs. LOD after drying was 1.8%, and the product was discharged (31.5 kg) in 74.8% yield (expected 60-90%). HPLC showed 100% purity.

What is claimed is:
1. A method of preparing a compound of Formula I

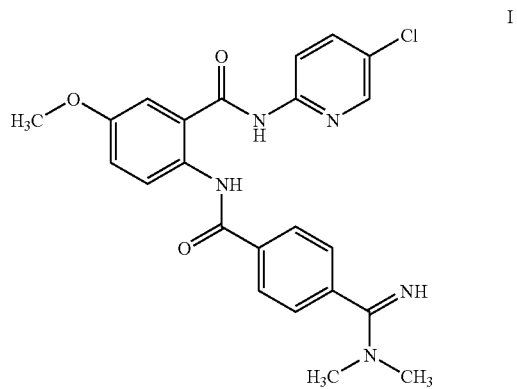

or a salt thereof, which method comprises contacting LiN(CH$_3$)$_2$ with a compound of Formula F:

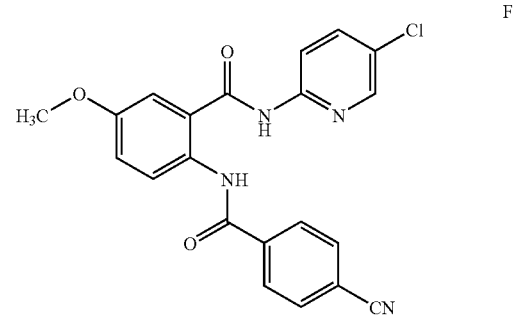 [SMILES: COc1ccc(NC(=O)c2ccc(C#N)cc2)c(C(=O)Nc2ccc(Cl)cn2)c1]

or a salt thereof, under conditions to form the compound of Formula I, and optionally contacting the compound of Formula I with an organic or inorganic acid to form a salt of the compound of Formula I.

2. The method of claim 1, wherein the reaction conditions to form the compound of Formula I comprise an aprotic solvent.

3. The method of claim 2, wherein the aprotic solvent is selected from the group consisting of tetrahydrofuran, diethyl ether, dimethoxymethane, dioxane, hexane, methyl tert-butyl ether, heptane, cyclohexane and mixtures thereof.

4. The method of claim 3, wherein the aprotic solvent is tetrahydrofuran.

5. The method of claim 1, wherein the contacting of LiN(CH$_3$)$_2$ with the compound of Formula F or a salt thereof is carried out under reaction conditions to afford the compound of Formula I in a yield of at least 75%.

6. The method of claim 1, wherein the LiN(CH$_3$)$_2$ is prepared by contacting dimethylamine with alkyllithium under reaction conditions.

7. The method of claim 1, wherein the compound of Formula F or a salt thereof is prepared by contacting a compound of Formula D:

D with a compound of Formula E:

E under reaction conditions to form the compound of Formula F or a salt thereof.

8. The method of claim 7, wherein the reaction conditions to form a compound of Formula F comprise tetrahydrofuran as a solvent.

9. The method of claim 7, wherein the contacting of the compound of Formula D with the compound of Formula E is carried out under reaction conditions to afford the compound of Formula F or a salt thereof in a yield of at least 70%.

10. The method of claim 7, wherein the compound of Formula D is prepared by exposing a compound of Formula C:

C to reaction conditions to form the compound of Formula D.

11. The method of claim 10, wherein the reaction conditions to form a compound of Formula D comprise hydrogen gas in the presence of a catalyst.

12. The method of claim 11, wherein the catalyst is sulfided 5% platinum on carbon.

13. The method of claim 11, wherein the reaction conditions to form a compound of Formula D comprise a temperature of between 19° C. and 28° C.

14. The method of claim 11, wherein the reaction conditions to form a compound of Formula D comprise a solvent selected from the group consisting of methylene chloride, ethanol, methanol, and ethyl acetate.

15. The method of claim 11, wherein the conditions to form a compound of Formula D comprise methylene chloride as a solvent.

16. The method of claim 11, wherein the compound of Formula D is afforded in a yield of at least 80%.

17. The method of claim 10, wherein the compound of Formula C is prepared by contacting a compound of Formula A:

A with a compound of Formula B:

B under reaction conditions to form the compound of Formula C.

18. The method of claim 17, wherein the reaction conditions to form a compound of Formula C comprise a temperature of between 19° C. to 28° C.

19. The method of claim 17, wherein the reaction conditions to form a compound of Formula C comprise acetonitrile as a solvent.

20. The method of claim 17, wherein the reaction conditions to form a compound of Formula C comprise phosphorous oxychloride and pyridine.

21. The method of claim 17, wherein the contacting of the compound of Formula A with the Compound of Formula B is carried out under reaction conditions to afford the compound of Formula C in a yield of at least 84%.

22. A method of preparing a compound of Formula I:

I or a salt thereof, comprising:
a) contacting a compound of Formula A:

A with a compound of Formula B:

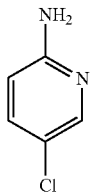

B under reaction conditions comprising acetonitrile as a solvent to form a compound of Formula C:

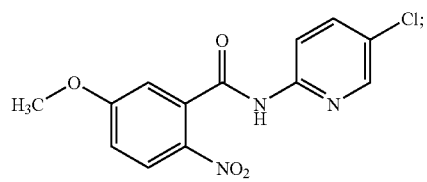

C b) exposing the compound of Formula C to reaction conditions to form a compound of Formula D:

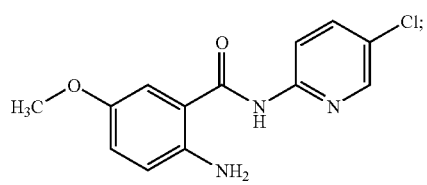

D c) contacting the compound of Formula D with a compound of Formula E:

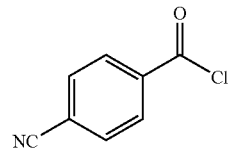

E under reaction conditions to form a compound of Formula F:

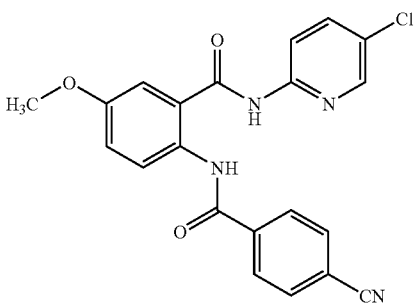

F or a salt thereof; and d) contacting $LiN(CH_3)_2$ with the compound of Formula F or a salt thereof, under reaction conditions to form the compound of Formula I, and optionally contacting the compound of Formula I with an organic or inorganic acid to form a salt of the compound of Formula I.

23. The method of claim 1 or claim 22, wherein the compound of Formula I or the salt of the compound of Formula I is prepared on a kilogram scale.

\* \* \* \* \*